(12) United States Patent
Weiss et al.

(10) Patent No.: US 8,014,575 B2
(45) Date of Patent: Sep. 6, 2011

(54) AUTOMATED NEUROAXIS (BRAIN AND SPINE) IMAGING WITH ITERATIVE SCAN PRESCRIPTIONS, ANALYSIS, RECONSTRUCTIONS, LABELING, SURFACE LOCALIZATION AND GUIDED INTERVENTION

(76) Inventors: Kenneth L. Weiss, Cincinnati, OH (US); Judd M. Storrs, Cincinnati, OH (US)

( * ) Notice: Subject to any disclaimer, the term of this patent is extended or adjusted under 35 U.S.C. 154(b) by 1078 days.

(21) Appl. No.: 10/598,764

(22) Filed: Sep. 11, 2006

(65) Prior Publication Data

US 2007/0223799 A1 Sep. 27, 2007
US 2011/0123078 A9 May 26, 2011

Related U.S. Application Data

(63) Continuation-in-part of application No. PCT/US2005/008311, filed on Mar. 11, 2005.

(60) Provisional application No. 60/552,332, filed on Mar. 11, 2004.

(51) Int. Cl.
*G06K 9/00* (2006.01)
*A61B 5/103* (2006.01)

(52) U.S. Cl. ...................... 382/128; 600/594

(58) Field of Classification Search .................. 382/100, 382/128, 129, 130, 131, 132, 133, 134, 168, 382/171, 173, 181, 224; 607/2, 43, 116, 607/117; 128/920; 345/418, 419, 424; 600/594; 378/1, 37, 21, 41, 42, 38, 44, 51, 62, 65, 378/146

See application file for complete search history.

(56) References Cited

U.S. PATENT DOCUMENTS

| | | | | |
|---|---|---|---|---|
| 4,294,577 A | * | 10/1981 | Bernard | 8/488 |
| 5,020,088 A | * | 5/1991 | Tobin | 378/164 |
| 5,270,654 A | * | 12/1993 | Feinberg et al. | 324/309 |
| 5,593,381 A | * | 1/1997 | Tannenbaum et al. | 601/93 |
| 5,971,968 A | * | 10/1999 | Tu et al. | 604/264 |
| 6,002,959 A | * | 12/1999 | Steiger et al. | 600/425 |
| 6,011,061 A | * | 1/2000 | Lai | 514/492 |
| 6,023,495 A | | 2/2000 | Adler et al. | |
| 6,240,308 B1 | * | 5/2001 | Hardy et al. | 600/407 |

(Continued)

OTHER PUBLICATIONS

Long et al., "Landmarking and feature localization in spine x-rays", J. Electron. Imaging, vol. 10, Issue 4, pp. 939-956, Oct. 2001.*

(Continued)

*Primary Examiner* — Andrew W Johns
*Assistant Examiner* — Tahmina Ansari
(74) *Attorney, Agent, or Firm* — Mark F. Smith; Smith Brandenburg Ltd.

(57) ABSTRACT

Automated spine localizing, numbering and autoprescription system enhances correct location of diseased or injured tissue, even allow multi-spectral diagnosis. Externally located this tissue is facilitated by an integrated self adhesive spatial reference and skin marking system that is designed for a variety of modalities to include MRI, CT, SPECT, PET, planar nuclear imaging, radiography, XRT, thermography, optical imaging and 3D space tracking. The device ranges from a point localizer to a more multifunctional and complex grid/phantom system. The specially designed spatial reference(s) is affixed to an adhesive strip with corresponding markings so that after applying the unit to the skin/surface and imaging, the reference can be removed leaving the skin appropriately marked. The localizer itself can also directly adhere to the skin after being detached from the underlying strip. A spine autoprescription process performs image analysis that is able to identify vertebrae and discs even in the presence of abnormalities.

30 Claims, 28 Drawing Sheets

U.S. PATENT DOCUMENTS

| | | | |
|---|---|---|---|
| 6,853,741 | B1 | 2/2005 | Ruth et al. |
| 2002/0004632 | A1 | 1/2002 | Lindquist et al. |
| 2003/0086596 | A1* | 5/2003 | Hipp et al. .................... 382/128 |
| 2003/0086599 | A1* | 5/2003 | Armato et al. ................ 382/131 |
| 2005/0228250 | A1* | 10/2005 | Bitter et al. ................... 600/407 |
| 2006/0122483 | A1* | 6/2006 | Foley et al. ................... 600/407 |
| 2006/0241368 | A1* | 10/2006 | Fichtinger et al. ............ 600/407 |
| 2008/0044074 | A1* | 2/2008 | Jerebko et al. ................ 382/128 |
| 2008/0132784 | A1* | 6/2008 | Porat et al. ................... 600/426 |

OTHER PUBLICATIONS

Archip et al., "A knowledge-based approach to automatic detection of the spinal cord in CT images", IEEE Transactions on Medical Imaging, vol. 21, No. 12, Dec. 2002.*

Kang et al., "A new accurate and precise 3-D segmentation method for skeletal structures in volumetric CT data", IEEE Transactions on Medical Imaging, vol. 22, No. 5, May 2003, pp. 586-598.*

"Rubidium Chloride (MSDS)", Fisher Scientific Material Safety Data Sheet, a Fischer Scientific International Company, Created Dec. 12, 1997, Revision #4, Date Mar. 18, 2003, Downloaded Jan. 14, 2010.*

International Search Report, PCT/US05/0311, Jul. 19, 2005, pp. 1-2.

Li, Z. et al., "Fast Decomposition of Water and Lipid Using a GRASE Technique With the Ideal Algorithm," Magnetic Resonance in Medicine, vol. 57 (2007) pp. 1047-1057.

Oshio, K. et al., Abstract of "GRASE gradient and spin-echo) imaging: a novel fast MRI technique," Magn. Reson. Med., vol. 20 (1991) pp. 344-349.

Outwater, E.K. et al., "Detection of Lipid in Abdominal Tissues with Opposed-Phase Gradient-Echo Images at 1.5 T: Techniques and Diagnostic Importance," RadioGraphics, vol. 18 (1998) pp. 1465-1480.

Reeder, S.B. et al., "Multicoil Dixon Chemical Species Separation With an Iterative Least-Squares Estimation Method, Magnetic Resonance in Medicine," vol. 51 (2004) pp. 35-45.

Yu, H. et al., "IDEAL Water-Fat Separation with Simultaneous T2* Estimation," Proc. Intl. Soc. Mag. Reson. Med., 14$^{th}$ Meeting (2006) p. 624.

* cited by examiner

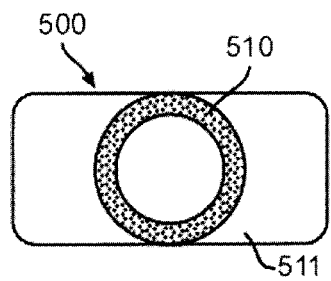 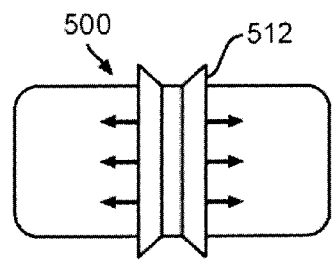
FIG. 14A    FIG. 14B
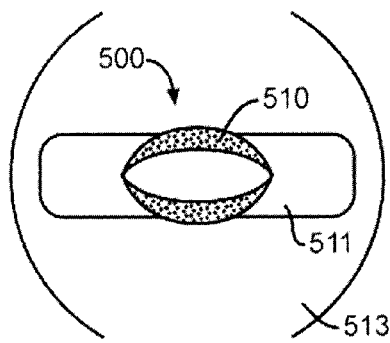 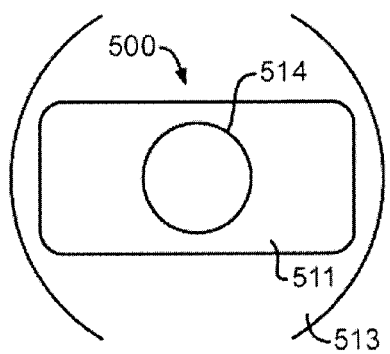
FIG. 14C    FIG. 14D
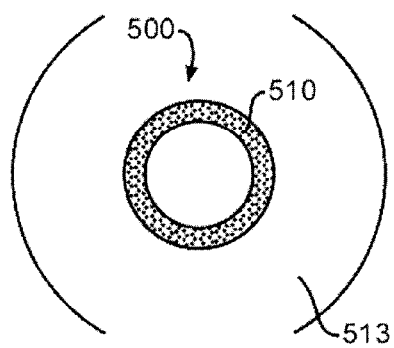 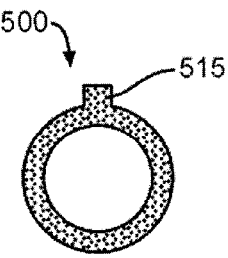
FIG. 14E    FIG. 14F

Figure 15A

| Distance | (+) | (-) |
|---|---|---|
| 0 | | |
| 1/2 | o ∘ o | o    o |
| 1 | o | o |
| 1 1/2 | ∞ | ∞ |
| 2 | ∞ | ∞ |
| 2 1/2 | ∞∘ | ∘∞ |
| 3 | ∞o | ∞o |
| 4 | ∞oo | ∞oo |
| 5 | o | o |
| | (Space Above Skin) | |
| 6 | 8 | 8 |
| 7 | 8o | o8 |
| 8 | 8∞ | ∞8 |
| 9 | 8∞o | o∞8 |
| 10 | ∞ | ∞ |
| 11 | 8/8 | 8/8 |
| 12 | 88 | 88 |
| 13 | 88o | o88 |
| 14 | 88∞ | ∞88 |
| ⋮ | | |
| 24 | 8888 | 8888 |

FIG. 15B 90 x 10 cm Grid Localizer

Sheath For 6-Element Array Coil

AUTOMATED NEUROAXIS (BRAIN AND SPINE) IMAGING WITH ITERATIVE SCAN PRESCRIPTIONS, ANALYSIS, RECONSTRUCTIONS, LABELING, SURFACE LOCALIZATION AND GUIDED INTERVENTION

CROSS REFERENCE TO RELATED APPLICATIONS

The present application is a continuation-in-part of and claims the benefit of PCT Patent Application, International Application No. PCT/US2005/008311, having an International filing date of 11 Mar. 2005 and designating the United States, which in turn claims benefit of U.S. Provisional Patent Application, having Ser. No. 60/552,332, filed 11 Mar. 2004, the disclosures of which are hereby incorporated by reference in their entirety.

FIELD

The present invention relates, in general, to medical diagnostic imaging devices that perform scout scans for localization and autoprescription and treatment and diagnosis of the neuro-axis.

BACKGROUND

Diagnostic imaging of the spine of a patient is often useful for identifying disease or an injury to the spine itself or as a readily locatable landmark for other tissues. Present practice is to take and digitally store lots of data on a patient, including MR and CT images. You want to both compare each patient's data to his/her own data, and "pools" of data from other people. However, making sense of pictures taken at different times, and using different types of machines presents a problem which is presently beyond the reach of most automated systems. Additional complications are presented by variations in quality between images, incomplete images of the spine or neuro-axis (e.g., an image might not include top or bottom vertebrae), failure to adequately capture portions of the neuro-axis due to congenital defect, disease, injury or surgery, exceptional curvature of the spine exhibited in some individuals, and the existence of individuals having more or less than the highly prevalent 23 mobile pre-sacral vertebrae. Thus, analysis of images and prescription of additional data collection and treatment requires an extensively trained technician.

Unfortunately, even for skilled technicians, human error may occur due to the variability in the patient population or due to an oversight. The mistake may arise in incorrectly identifying vertebrae and discs in a diagnostic image. The mistake may arise in incorrectly visually identifying the corresponding vertebrae under the skin before performing a surgical or therapeutic (e.g., radiation) treatment. The mistake may arise in improperly identifying a normal, benign, or malignant condition because an opportunity is missed to correctly correlate information from a plurality of imaging systems (e.g., a type of tissue may be determined if an MRI and a CT image could be properly correlated and analyzed).

Assuming the vertebrae and discs may be accurately identified in the diagnostic image, it is often helpful to be able to obtain a one-to-one correspondence between the readily visible and markable skin/surface and underlying structures or pathology detectable by a variety of imaging modalities. This may facilitate clinical correlation, XRT, image guided biopsy or surgical exploration, multimodality or interstudy image fusion, motion correction/compensation, and 3D space tracking. However, current methods, (e.g. bath oil/vitamin E capsules for MRI), have several limitations including single image modality utility requiring completely different and sometimes incompatible devices for each modality, complicating the procedure and adding potential error in subsequent multimodality integration/fusion. They require a separate step to mark the skin/surface where the localizer is placed and when as commonly affixed to the skin by overlying tape, may artifactually indent/compress the soft tissue beneath the marker or allow the localizer to move, further adding to potential error. Sterile technique is often difficult to achieve. Furthermore, it may be impossible to discriminate point localizers from each other or directly attain surface coordinates and measurements with cross sectional imaging techniques. In regards to the latter, indirect instrument values are subject to significant error due to potential inter-scan patient motion, nonorthogonal surface contours, and technique related aberrations which may not be appreciated as current multipurpose spatial reference phantoms are not designed for simultaneous patient imaging.

Limited coverage, resolution and contrast of conventional MRI localizers coupled with a high prevalence of spinal variance make definitive numbering difficult and may contribute to the risk of spinal intervention at the wrong level. Only 20% of the population exhibit the classic 7 cervical, 12 thoracic, 5 lumbar, 5 sacral, and 4 coccygeal grouping. For instance, 2-11% of individuals have a cephalad or caudal shift of lumbar-sacral transition, respectively resulting in 23 or 25 rather than the typical 24 mobile presacral vertebrae. Numbering difficulties are often heightened in patients referred for spine MRI. Such patients are more likely than the general population to have anomalies, acquired pathology, or instrumentation that distorts the appearance of vertebrae and discs. Moreover, these patients are often unable to lie still within the magnet for more than a short period of time due to a high prevalence of back pain and spasms. Resultant intrascan motion confounds image interpretation and interscan motion renders scan coordinates and positional references unreliable.

Those difficulties and inadequacies in presently available technology can lead to significant problems. While data remains somewhat limited, various authors report an approximately 2-5% incidence of wrong level approach spinal intervention, with most cases involving the lower lumbar interspaces. Such surgical misadventures may lead to needless pain and suffering, as well as contribute to accelerating medical malpractice costs. The first multi-million dollar jury verdict for such a wrong level approach was awarded in 2002. In addition to potentially introducing errors, the use of human technicians to analyze images in present technology leads to significant delays and cost increases in diagnosis. For example, in the case of an image where insufficient information has been gathered by an initial scan, such as a scout scan, a human technician would examine the initial images, then prescribe new images, then would have to analyze the new images as well, leading to the necessity for images to be taken in multiple sessions over a longer period of time, a more complicated and expensive process than would be desirable.

Although several research techniques have been described to automate spine image analysis, to the inventors' best knowledge, none has successfully addressed the need for accurate and unambiguous numbering. In some cases, the inadequacies might be caused by simplifying assumptions based on normal spine anatomy which might not be appropriate for patients referred for spinal imaging (e.g., U.S. Pat. No. 6,853,741 to Ruth et al., which assumes that the distance between vertebrae is substantially constant). In others, inadequacies might stem from the fact that, even if an individual vertebra can be located, characterization of a vertebrae or disc is of limited clinical value if that structure can not be accurately identified and named.

Consequently, a significant need exists for an improved approach to localizing and autoprescribing through multimodal quick scans of the brain and/or spine. Furthermore, there is a need for enhancing personal medicine with a method of aligning skull and spine images.

Once one image set is autoprescribed, it would be further beneficial to correlate that image set with other types of imaging modalities that are also autoprescribed. One advantage is that calculations of changes over time for the same patient may quickly identify injury or disease. Another advantage is that different spectral emissions illicit different information about a tissue. Correlating between a plurality of imaging modalities, if a common tissue structure can be localized for each, may enable autodiagnosis as to whether the tissue is normal, benign or malignant. Consequently, it would be of a further advantage to extend spine autoprescription across multiple sources of diagnostic images.

Additionally, if a volume imaging data set is obtained it may be beneficial to have automated optimized 2-D reformations with labeling as desired to facilitate interpretation.

SUMMARY

The present invention addresses these and other problems in the prior art by providing an apparatus and method of localizing a spinal column of a patient with robust automated labeling of vertebrae across a population and across different imaging modalities facilitating autoprescription and follow-on therapeutic procedures. Thereby, human error in incorrectly identifying a vertebra in an image, and thus mislocating a surgical site, is avoided.

In one aspect of the invention, an apparatus processed a medical diagnostic image of a patient's torso by identifying voxel clusters of appropriate size, location, shape, orientation, and intensity to be putative spinal structures. Then additional constraints are applied to identify a long chain of spinal structures that are then labeled.

In another aspect of the invention, this processing is in conjunction with a localizer grid placed on the torso of the patient that provides an external reference correlated to the identification and labeling, enabling accurate insertion or aiming of therapeutic treatments.

In another aspect of the invention, related to MRI, a flexible array surface coil overlies the spine (potentially in conjunction with the aforementioned localizer grid) to increase the signal to noise ratio and afford optimal spine imaging in any patient position.

By virtue of the foregoing, an entire spine can be effectively surveyed with sub-millimeter in-plane resolution MRI or multi-detector CT in less than one minute. All cervical-thoracic-lumbar vertebrae and discs can be readily identified and definitively numbered by visual inspection. All cervical-thoracic-lumbar vertebrae and discs can be readily identified and definitively numbered by semi-automated computer algorithm. Rapid technique should facilitate accurate vertebral numbering, improve patient care, and reduce the risk of surgical misadventure. Coupled with an integrated head and spine array coil, rapid computer automated iterative prescription and analysis of the entire neuro-axis may be possible.

These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIGS. 14A-14I are diagrams of a point localizer; FIG. 14A depicts a frontal view of the point localizer affixed to fabric; FIG. 14B depicts a reverse side of the point localizer of FIG. 14A; FIG. 14C is a perspective view of the point localizer and underlying fabric affixed to the skin; FIG. 14D is an enface view of the fabric with corresponding marking affixed to the skin; FIG. 14E is an enface view of the localizer affixed to skin; FIG. 14F is a diagram view of a port integrated into a tubular ring; FIG. 14G is a frontal view of a modified ring shaped localizer affixed to fabric with additional markings; FIG. 14H is a frontal view of the fabric in FIG. 14G with the localizer removed; FIG. 14I is a frontal view of a multilocalizer sheet demonstrating the adhesive backing and overlying fabric with localizers removed.

FIGS. 15A-15F illustrate a cross-shaped grid configuration; FIG. 15A is an enface view of the grid with modified square as the central hub and uniquely positioned rows of tubing radiating along the vertical and horizontal axes; FIG. 15B is a schematic of axial cross sections acquired at representative distances from the horizontal axis; FIG. 15C demonstrates the underlying marked fabric with the superimposed tubing in FIG. 15A removed; FIG. 15D is a variant of FIG. 15A with modified ring serving as a central hub; FIG. 15E depicts a limb fixation ring and angulation adjuster; and FIG. 15F depicts a radiopaque grid with underlying ruled fabric strips removed.

DETAILED DESCRIPTION

Spine localization, automated labeling, optimized reconstructions, and data fusion diagnostic system.

Figure 1:
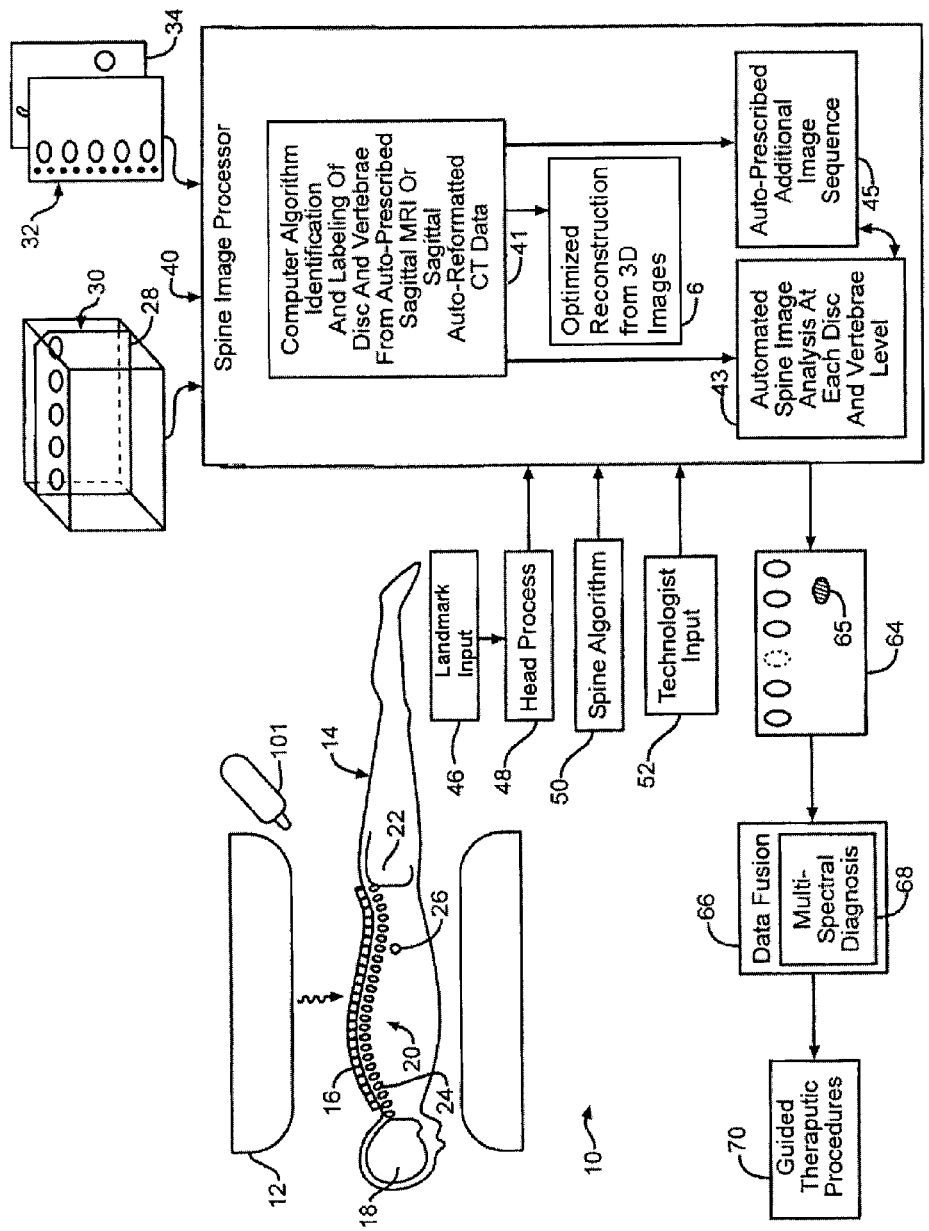
FIG. 1 is a diagram of an automated spinal diagnostic system.

FIG. 1 depicts an automated spinal diagnostic system 10. The system depicted in FIG. 1 includes a diagnostic imaging system 12, which is a system such as a magnetic resonance imaging system (MRI), or a computed tomography (CT) scanner that is capable of producing a representation of a portion (it should be understood that, in the context of this paper, a portion could be the entire patient) of a patient. Such a representation might be used to create an image which can be examined by a physician or technologist, such as a digital image displayed on a screen or a physical image printed on film, or it might be stored internally in a computer's memory and used to automate or partially automate the treatment of a patient. For the purpose of clarity, when terms such as "imaging system" and "diagnostic image" are used in this paper, it should be understood that those terms are not intended to be limited externally visible images (e.g., an image on film) and systems which produce them, but are instead intended to encompass systems which produce representations which are used in a computer's internal processes and which are not necessarily displayed to a physician or technologist. Similarly, when the term "label" is used in this paper, it should be understood to refer not only to a visible label, but to any signifier which can be used for unique and consistent identification. In FIG. 1, the diagnostic imaging system 12 is used to image a torso of a patient 14. As depicted in FIG. 1, the torso of a patient 14 is advantageously covered by a skin/surface marking system 16. In some embodiments, the skin/surface marking system 16 might serve as an integrated multimodality, multi-functional spatial reference. That is, the skin/surface marking system 16 might be designed in such a way as to be visible in medical diagnostic images produced by different imaging modalities (e.g., CT scan, MRI system), and might also be designed in such as away as to achieve multiple functions (e.g., to produce a visible representation in the medical diagnostic image and to leave a marking on the patient's skin or some other surface). In an embodiment following the diagram of FIG. 1, the diagnostic imaging system 12 might produce one or more medical diagnostic images depicting the patient's skull 18, the patient's full spine 20, and/or the patient's pelvic bones 22. In some embodiments, the diagnostic imaging system serves to perform an automated MRI technique that rapidly surveys the entire spine, labeling all discs (flattened anatomical structures which lie between adjacent vertebrae in the spine) and vertebrae (the bones or cartilaginous segments forming the spinal column). While being tested, the illustrative version described below was able to survey the entire spine with sub-millimeter in-plane resolution MRI in less than 1 minute. C-T-L vertebrae and discs can be readily identified and definitively numbered by visual inspection or semi-automated computer algorithm ("ASSIST").

Correctly identifying each spinal structure, that is, each vertebra or disc, in the spine 20 is complicated in certain instances when the skull 18 and/or the pelvic bones 22 are not imaged. In some instances, a vertebra or disc (depending on whether CT, MRI, or some other imaging modality, is being used) will fail to image properly, depicted at 24. In addition, the highly predominant number of twenty-four mobile presacral vertebrae may not be the case for certain individuals. Having the correct vertebrae references may be important in localizing a suspicious lesion 26, which might be later targeted by some type of therapeutic instrument, that is any tool or device which can be used to help improve or restore health. A non-limiting example of such a therapeutic instrument is the radiation device 101 depicted in FIG. 1.

The diagnostic imaging system 12 may derive a sagittal image 28, that is, an image of a plane parallel to the median plane of the body, of the torso of the patient 14 from a volume CT scan 30 (also called a sagittal section). Alternatively, the diagnostic imaging system 12 may produce an upper cervical-thoracic sagittal image 32 and a lower thoracic-lumbar sagittal image 34, such as from MRI. In this application, a thoracic lumbar sagittal image should be understood to mean a sagittal image which includes a representation of the bottom (inferior) portion of the spine, while the term cervical thoracic sagittal image should be understood to mean a sagittal image which includes a representation of the top (superior) portion of the spine. In some embodiments following the diagram of FIG. 1, a spine image processor 40, which may be a process hosted by the diagnostic imaging system 12 or by a remote device, performs a number of subprocesses to correctly identify and label the spine 20.

In an illustrative version of the diagnostic imaging system 12, MRI studies were performed on a clinical 1.5 T magnet with standard 4-channel quadrature array 6-element spine coil and surface coil correction algorithm. Contiguous two-station 35 centimeter (cm) field of view (FOV) sagittal fast gradient-recalled echo (FGRE) sequences were pre-programmed, providing full cervical, thoracic and lumbar (C-T-L) spine coverage. Combined sagittal FOV of 70 cm., 7 sections, scans from 15 millimeters left of midline to 15 millimeters right of midline (L15-R15), 4 millimeter (mm) section thickness with 1 mm intersection gap; 512×352 matrix, 1 excitation/image acquisition (nex), repetition time (in milliseconds) (TR) 58, echo time (in milliseconds) (TE) 2.0, 30° flip, Bandwidth (BW) 15.6 kHz; 21 sec×2 stations=42 sec. To facilitate and standardize auto-prescriptions, a line was drawn on the spine coil for the technologists to landmark (set as scanner's 0 coordinate) rather than have the technologist use a superficial anatomic feature. The coil has a contoured head/neck rest assuring grossly similar positioning of the cranial-cervical junction of each patient relative to this landmark. The semi-automated disc detection and numbering algorithm of the spine image processor 40 was iteratively developed, tested and refined on batches of consecutive de-identified patient studies and results compared to neuroradiologist assignments. The spine image processor 40 was implemented in MATLAB 7.

In block 41, a computer algorithm is hosted on the spine image processor for the identification and labeling of disc and vertebrae from auto-prescribed sagittal MRI or sagittal auto-reformatted CT data, described in greater detail below. This information may be advantageously provided to an automated spine image analysis algorithm 43 that further characterizes each disc and/or vertebrae level. Alternatively or in addition, this information from block 41 may be advantageously provided to an auto-prescription algorithm 45 for additional image sequences, utilizing the identified spinal landmarks as references. Further, the additional processes 43, 45 may exchange information with each other, such as detained analysis and diagnosis of a particular vertebra in block 43 being enabled by auto-prescribed detailed images in block 45.

These analyses performed by the spine image processor 40 in the illustrative version key upon one or more sources of information to identify a unique definable reference landmark for characterization and unambiguous labeling of one or more spinal structures. In the illustrative MRI embodiment, the centroid of the top (most cephalad) intervertebral disc (C2-3) is utilized as a key landmark. Alternatively, the top vertebrae (C1 or C2), or other unique identifiable structure, or other landmark may be employed.

In particular, in block 46, the top intervertebral disc is identified, which may be automated in block 48 by interfacing with an automated cranium identification system, such as described in U.S. patent application Ser. No. 10/803,700, "AUTOMATED BRAIN MRI AND CT PRESCRIPTIONS IN TALAIRACH SPACE" to Dr. Weiss, filed 18 Mar. 2004, the disclosure of which is hereby incorporated by reference in its entirety. Alternatively, logic may be incorporated into the spine image processor 40 wherein a spine algorithm in block 50 recognizes a top vertebra or intervertebral disc. As a further alternative and as fall back option should automated means fail, in block 52 a technologist input is received to identify the top vertebra or intervertebral disc.

Figure 9:
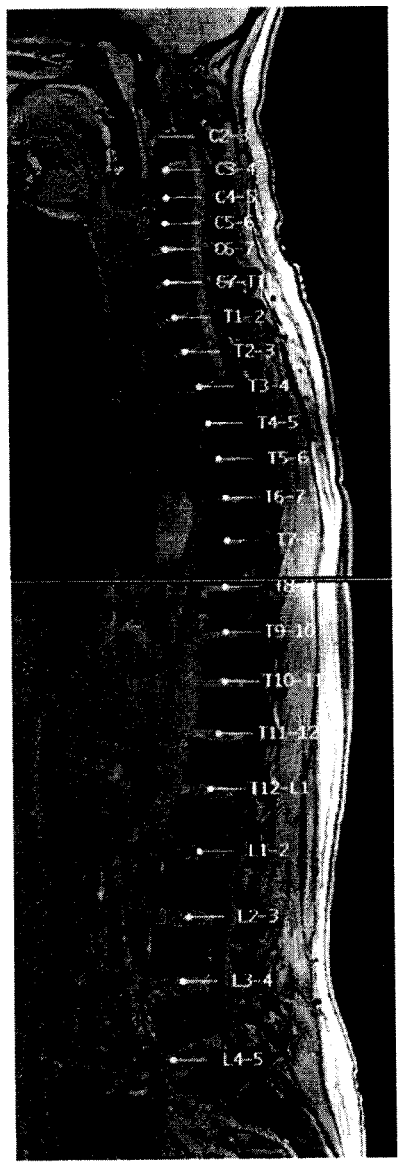
FIG. 9 is a sagittal image through the entire spine of a patient with 23 mobile/presacral vertebrae with correct auto-labeling of first 22 interspaces.
Figure 10:
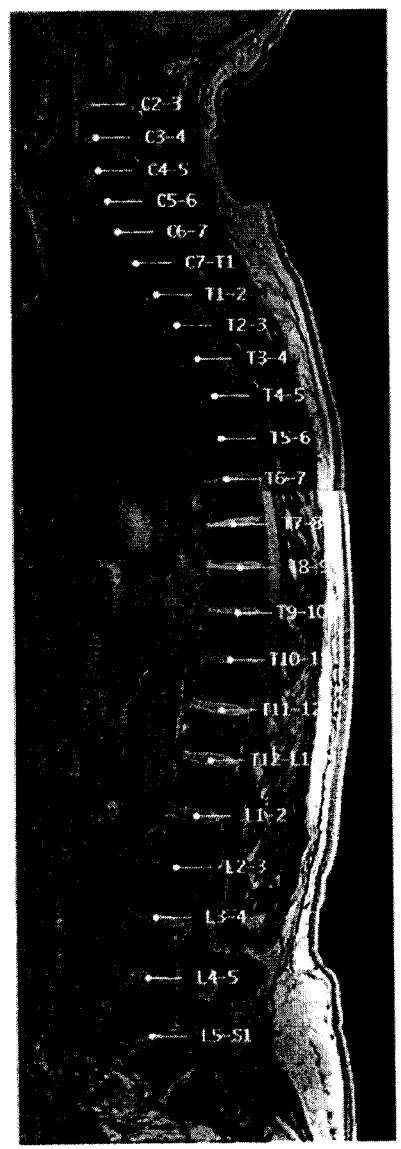
FIG. 10 is a sagittal image through the entire spine of a patient with 25 potentially mobile presacral vertebrae with correct auto-labeling of the first 23 interspaces.

During testing, the neuroradiologist could readily visualize and definitively number all cervical-thoracic-lumbar (C-T-L) levels on ASSIST localizers. 6/50 patients had a congenital shift in lumbar-sacral transition; 3 with 23 mobile pre-sacral vertebrae (as shown in FIG. 9) and 3 with 25 mobile pre-sacral vertebrae (as shown in FIG. 10). Based upon manual placement of a single seed in the C2-3 interspace, in the illustrative version with 50/50 cases performed by the spine image processor 40 the automated disc detection and numbering algorithm was concordant with neuroradiologist assignments in 50/50 (100%) of cases.

With a labeled disc image 64, correct relative location to other imaged tissue of interest 65 may be used for further diagnostic procedures or therapeutic intervention. For instance, data fusion (block 66) might allow images taken with the same type of imaging modality at different times to be correlated, which could facilitate monitoring growth progression of a suspicious lesion or changes due to an intervening injury. In addition, images taken with different imaging modalities might be cross referenced to perform multi-spectral diagnoses (block 68), wherein information on a type of tissue may be gained by its different responses to various types of electromagnetic spectra. With tissue diagnosis complete, in block 70 a guided therapeutic procedures algorithm may correctly orient a therapeutic agent, such as the radiation device 101 or a guided minimally invasive surgical instrument (not shown). Alternatively, for an externally oriented procedure, a surgeon may reference either the relative location to a known spinal structure (e.g., vertebrae) and/or reference the skin/surfacing marking system 16.

During testing of the illustrative algorithm, patients received a rapid total spine ASSIST localizer with pre-set parameters. All studies were performed on a 1.5 T GE Excite MRI system with standard 4-channel, 6-element quadrature spine coil and surface coil correction algorithm. Contiguous two-station 35 cm field of view (FOV) sagittal fast gradient-recalled echo (FGRE) sequences were pre-programmed, providing full cervical, thoracic and lumbar (C-T-L) spine coverage. Combined sagittal FOV was 70 cm., 7 sections were obtained at each station, L15-R15, 4 mm section thickness with 1 mm intersection gap; 512×352, 1 nex, TR 58, TE 2.0, 30° flip, BW 15.6; 21 sec×2 stations=42 sec. These ASSIST studies were de-identified in consecutive batches and copied to CD for subsequent off-line review, computer algorithm development and testing. A semi-automated disc detection and numbering algorithm was iteratively developed and results compared to neuroradiologist assignments.

During testing, a first batch of 27 cases was initially run with an algorithm 100 developed using previously obtained, non surface-coil corrected ASSIST images. As the first step 102, we input cervical thoracic (top half), and thoracic lumbar (bottom half) spines. A threshold and a median spatial filter are applied to the search region. Then, additional disc constraints are applied to identify longest chain in top and bottom images. Candidate discs must extend onto at least two adjacent slices. As used in this application, adjacent slices should be understood to refer to two slices for which the space between those slices is not represented in a medical diagnostic image. Objects at the boundary or touching the boundary of the search region are excluded. Different threshold values, and candidate discs' constraints are applied to the top, and bottom half image.

Figure 2:
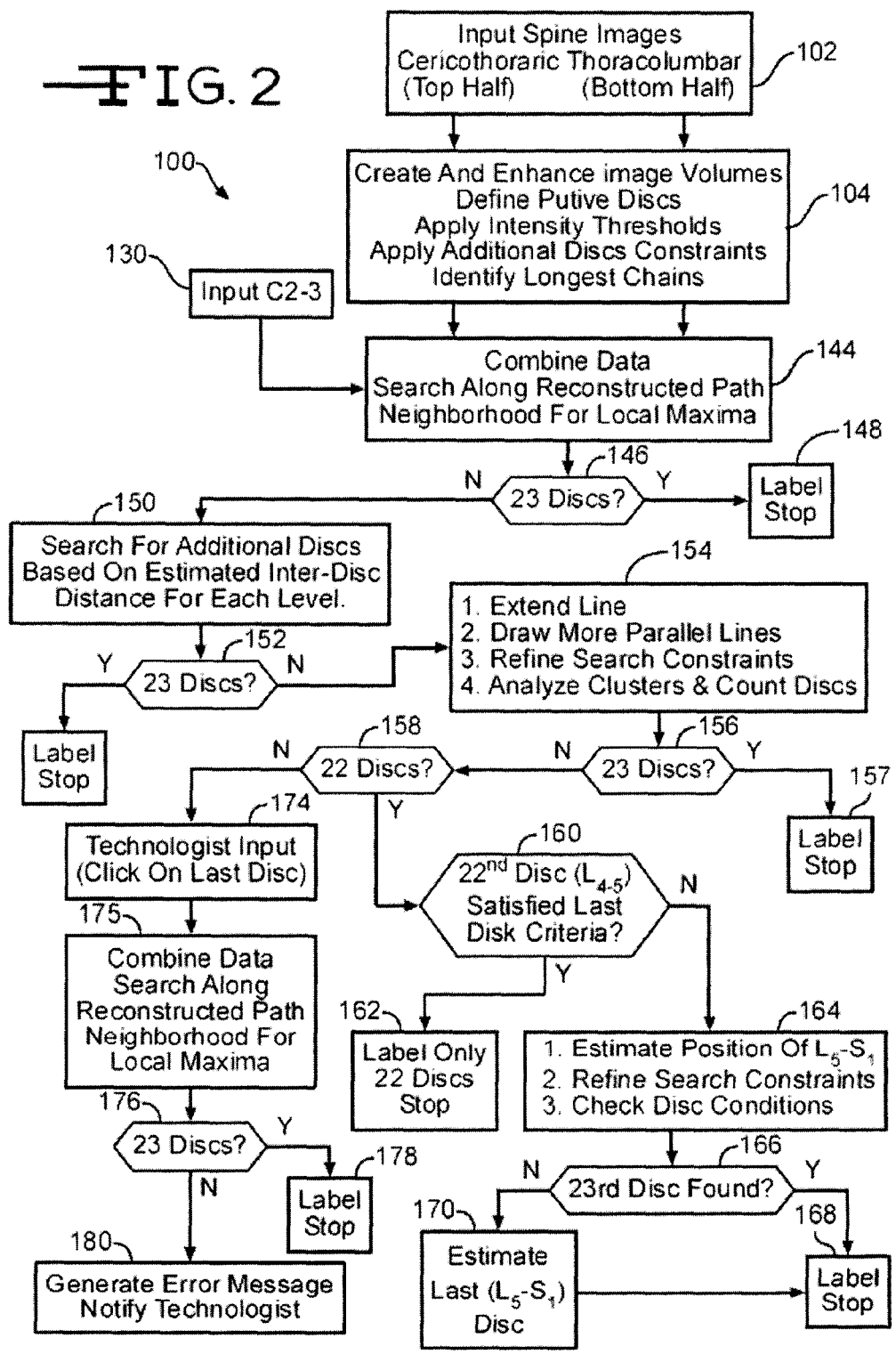
FIG. 2 is a flow diagram of a spine identification sequence of operations or procedure for the automated spinal diagnostic system of FIG. 1.

In FIG. 2, the automated disc detection and numbering algorithm 100 is a multi-step iterative process. DICOM (i.e., Digital Imaging and Communications in Medicine) ASSIST images of the cervical thoracic (top half), and thoracic lumbar (bottom half) spine are first input into MATLAB 7 (The Math Works, Inc., Natick, Mass.) for digital image processing (block 102). In the illustrative example, the digital image processing is based on analysis of voxels, or units of graphic information. In the illustrative example, because each medical diagnostic image represented a sagittal slice, the voxels represent locations in three dimensional space, though other embodiments might alternatively be based on analysis of locations in two dimensional space, or on other units of information.

Figure 5:
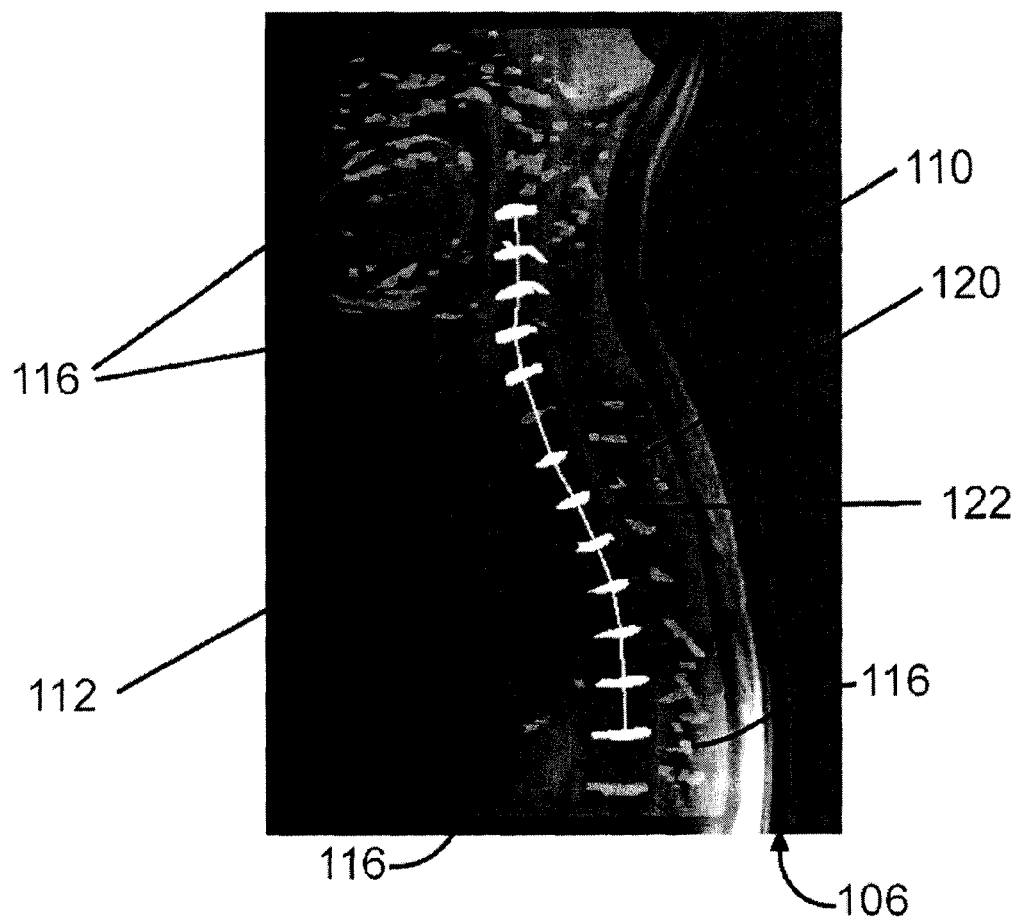
FIG. 5 is a 7-slice sagittal MRI projected image volume having a 35 cm FOV top half illustrating a typical search region where voxels exceeding an intensity threshold are depicted with those meeting additional disc constraints highlighted as putative discs and connected by a curved line through their centroids.
Figure 6:
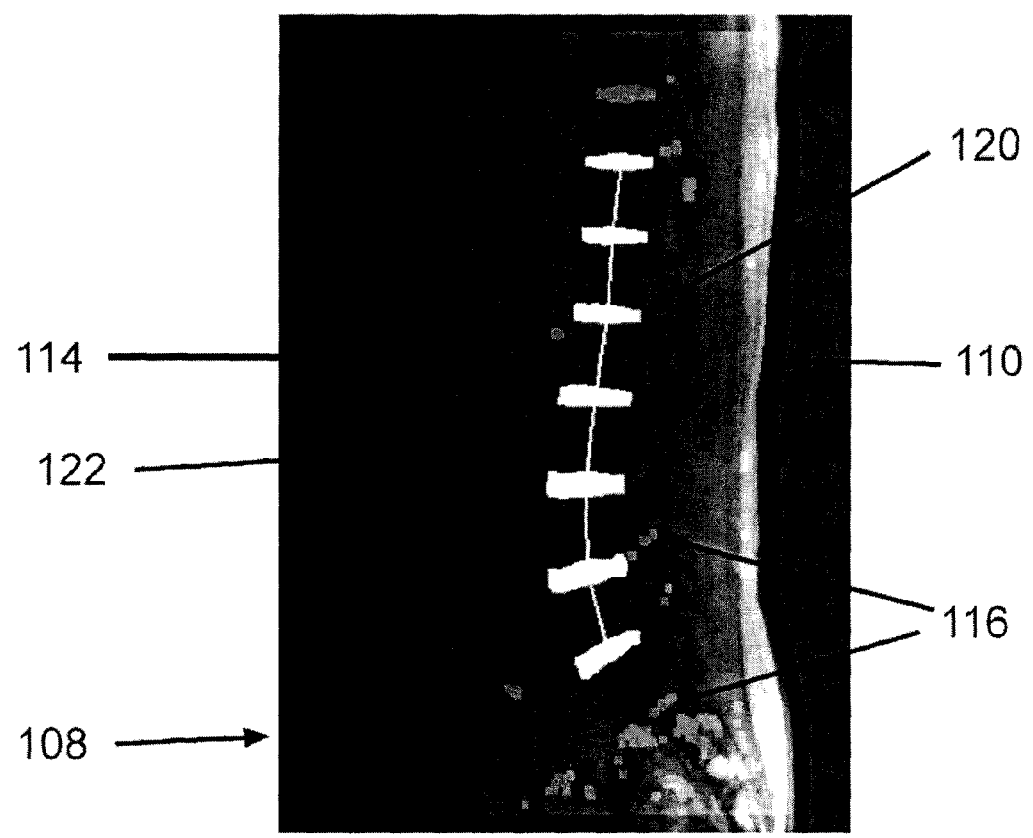
FIG. 6 is a 7-slice sagittal MRI projected image volume having a 35 cm FOV bottom half illustrating a typical search region wherein voxels exceeding intensity threshold are depicted with those meeting additional disc constraints highlighted as putative discs and connected by a curved line through their centroids.

Initially, the two data sets are processed to obtain putative discs separately, utilizing different threshold values and disc constraint parameters (block 104), with resulting upper and lower images 106, 108 depicted in FIGS. 5 and 6 respectively. As used in this application, a disc constraint should be understood to mean a criteria applied to determine whether a structure represented by a plurality of voxels is a spinal disc. Similarly, a spinal structure constraint should be understood to mean a criteria applied to determine whether a structure represented by a plurality of voxels is a spinal structure. The images 106, 108 are enhanced with a tophat filter and background noise is suppressed. A posterior edge 110 of the back is then identified in each image 106, 108 and search regions 112, 114 assigned respectively. The algorithm 100 thresholds and applies a median spatial filter to the search regions. Voxels 116 exceeding threshold values are then subjected to additional constraints.

Figure 3:
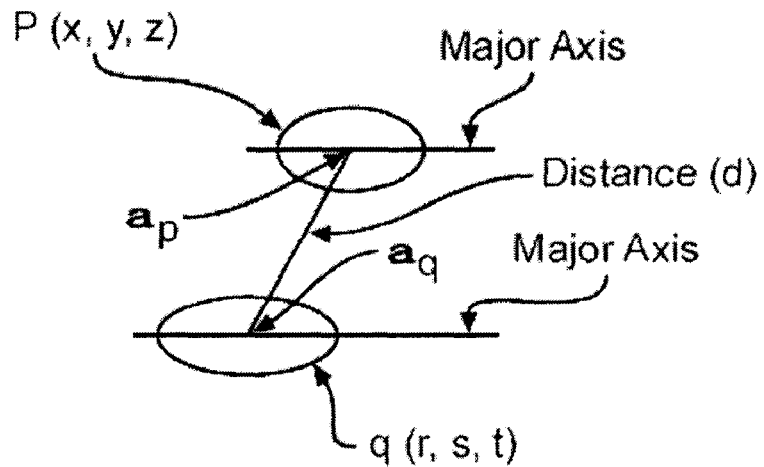
FIG. 3 is a diagram of a projection function of adjacent objects; $a_p$ and $a_q$ represent the angles between the line connecting candidate disc p and q through their centroid and the major axis of discs p and q respectively, wherein $0 < a_p < 90°$; let $d_c$ be the value of d for any candidate disc in cervical-thoracic spine region and $d_L$ in the thoracic-lumbar spine, then $6\,mm < d_c < 80\,mm$ and $8\,mm < d_L < 100\,mm$.
Figure 4:
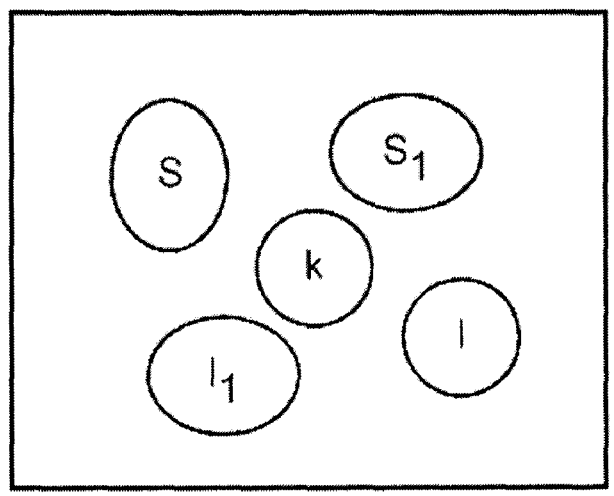
FIG. 4 is a diagram of distance constraint chains with a cluster, k, is part of a disc chain if its closest superior neighbor has k as its closest inferior neighbor and k's closest inferior neighbor has (k) as its closest superior neighbor.

Acceptable voxels must extend onto at least two adjacent sagittal sections but not touch the boundary of the search region 112, 114. The acceptable voxels must lie 6-80 mm in the cervical thoracic (C-T), and 8-100 mm in the thoracic lumbar (T-L) region from adjacent acceptable voxels. The centroids, that is, the voxels whose coordinates are determined by a weighted mean of the coordinates of the voxels in a voxel cluster, the weight of the coordinates being determined by an attribute such as intensity of the voxel at that coordinate, of these acceptable voxel clusters 120 (candidate discs) are then connected by curved line 122. The angle subtended by the line 122 connecting the centroid of adjacent candidate discs 120 and the major axis of these discs must be between 45° and 135° in both the C-T and T-L spine. In FIG. 3, projection analysis is used to constrain disc assignments. Furthermore, for a disc (k) to be considered part of a chain, its closest superior neighbor must have k as its closest inferior neighbor and k's closest inferior neighbor must have k as its closest superior neighbor. In FIG. 4, an angle relative to the major axis is evaluated to constrain disc assignments. The algorithm selects the longest disc chain in the C-T and T-L regions respectively (FIGS. 5, 6).

In block 130, the technologist is instructed to approximate (click on) the centroid of C2-3 at anytime during or before the aforementioned candidate disc evaluation. The centroid of C2-3 and the longest disc chains in the C-T and T-L spines are connected with a straight line. Using 3D linear interpolation, the program searches along this line and twelve adjacent parallel lines 140, represented by only four in FIG. 7 for clarity due to their superimposition in the sagittal projection. After applying Gaussian filters, the algorithm 100 finds local intensity maxima along each path (equivalently, the algorithm might also search for other extrema, such as local intensity minima, depending on the imaging modality and image data obtained). Points 142 that are less than 7.5 mm apart are grouped into clusters. These clusters are analyzed based on orientation, eccentricity, and spatial relationship relative to other clusters (block 144 of FIG. 2).

Figure 8:
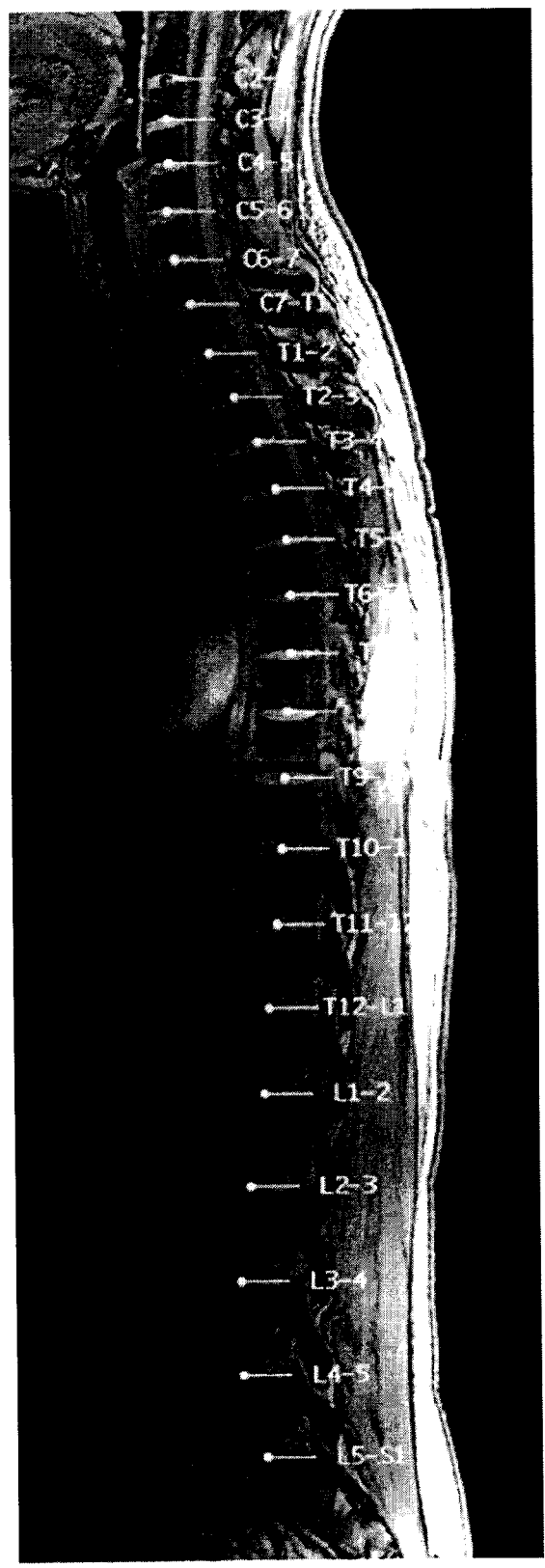
FIG. 8 is a sagittal image through the entire spine with all intervertebral discs auto-labeled with labeling of vertebrae omitted for clarity with three-dimensional (3-D) coordinates generated by an algorithm providing a means for discs or vertebral bodies to be labeled in any subsequent imaging plane providing no gross inter-scan patient movement.

Continuing with FIG. 2, if twenty-three (23) discs are selected in block 146, the computer auto-labels these discs or adjacent vertebrae and stops (block 148). The process of labeling discs or vertebrae might result in the production of images as depicted in FIGS. 8-10. Otherwise, search criteria and thresholds are refined based on estimated inter-disc height (h) for each disc level (L) using the following formula: (equation 1) h=0.6M for L=1, 2, or 3 and h=M+(L-1.2)*0.05M for L>3, where M (mean)=distance along line thru centroids/23.

In block 150, if 23 discs are not yet identified in block 146, the program 100 extends the search line inferiorly based on the estimated position $(E_{x,y})$ of the missing disc(s). (Equation 2)

$$E_{(x_j,y_j)} = (x_{j-1}, y_{j-1}) + h_a(x_{j-1}, y_{j-1}) \times \sum_{1}^{j-1} \frac{h_s(x, y)}{h_a(x, y)}$$

where $h_a$ is the average vertebral height from a 22 subject training set, $h_s$ is the vertebral height from the subject in question. The program searches for local maxima along this line extension and 24 adjacent parallel lines. A further determination is made in block 152 as to whether 23 discs have been found. Iteration continues as long as twenty-three (23) discs are not selected, as represented by block 154 that extends the search and the further determination of block 156, which labels the vertebrae if 23 are selected (block 157).

If not 23 discs in block 156, then in block 158 a further determination is then made that twenty-two (22) discs are selected. If so, the algorithm 100 will determine in block 160 whether the last identified level (L4-5) satisfies criteria for the terminal pre-sacral interspace suggesting a congenital variant with 23 rather than the typical 24 mobile presacral vertebrae. To be considered a terminal disc, the centroid of the $22^{nd}$ disc must lie within 25% of its expected location E(x, y) relative to the $21^{st}$ disc. Additionally, the centroid must lie posterior to the centroid of the $21^{st}$ disc and the slope of the $22^{nd}$ disc must be positive and greater than that of the $21^{st}$ disc. If those criteria are met, then twenty two discs will be labeled (block 162).

If 23 discs are found in block 166, the discs are labeled in block 168. Else, if the terminal disc criteria are not met in block 166, the position of the $23^{rd}$ (L5-S1) disc is estimated using Equation 2 (block 164), and search constraints refined. If the $23^{rd}$ disc is still not identified in block 166, the disc is presumed to be severely degenerated or post-surgical and the estimated position for L5-S1 will be accepted in block 170 and the discs thus labeled (block 168).

If less than 22 discs are identified by the algorithm in block 158, then the technologist will be instructed in block 174 to approximate (click on) the centroid of the last disc. The "combine data" step from block 144 is repeated in block 175 and if necessary the "search for additional discs" step as well. If twenty-three (23) discs are selected in block 176, then the discs are labeled in block 178. Else, if twenty three (23) discs are still not selected in block 176, the algorithm prints out, "Sorry, computer unable to detect all the discs. Require technologist revision." (block 180) Alternatively, rather than requesting technologist input, the computer could extract additional information from subsequently or concurrently obtained co-registered sequences such as the separate water and fat images depicted in FIG. 20a. Such multispectral segmentation may be more robust but require more time than segmentation algorithms relying on a single form of contrast.

Figure 7:
FIG. 7 is a combined sagittal image depicting search paths parallel to the curved line of FIG. 6 connecting a centroid of a C2-3 disc with longest disc chains from top and bottom half images (FIGS. 5 and 6). Dots correspond to local maxima along these paths.

The algorithm was run on an INTEL (San Jose, Calif.) personal computer with a 2.8 Ghz Xeon processor. Computer auto-labeling was compared to independent neuroradiologist assignments for each patient's study. The automated spine MRI sequencing provided a robust survey of the entire C-T-L spine in 42 seconds total acquisition time. In all patients (50/50), the neuroradiologist could readily visualize and definitively number all C-T-L levels on the ASSIST localizers. These included six patients with a congenital shift in their lumbar-sacral transition; three with 23 mobile pre-sacral vertebrae (FIG. 5) and three with 25 mobile pre-sacral vertebrae (FIG. 6). Several patients had post-operative spines to include metallic instrumentation (FIG. 7).

Figure 11:
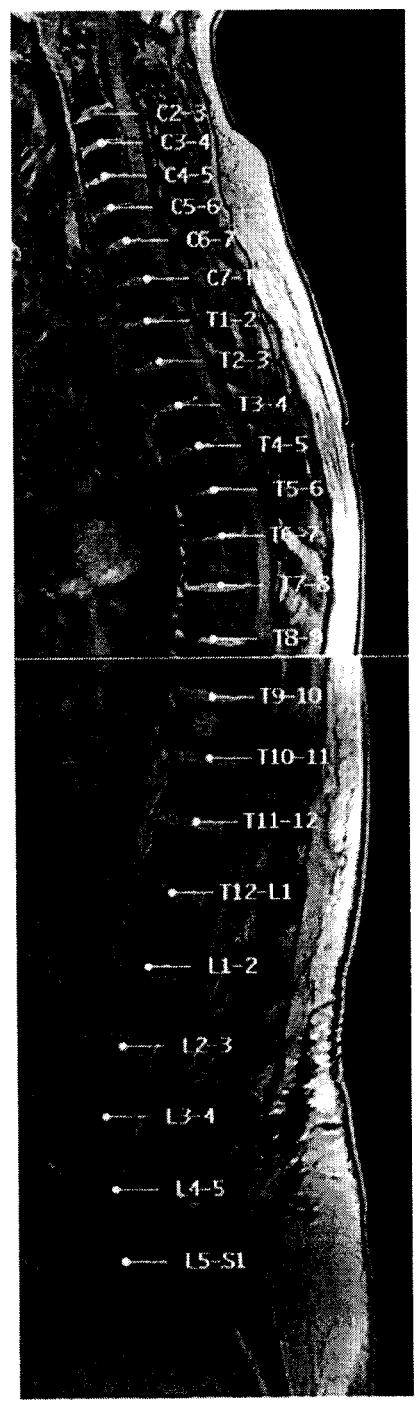
FIG. 11 is a sagittal image through the entire spine of a patient with surgically fused L4-5 interspace and associated artifact from a metallic cage with correct labeling of all 23 interspaces including a good approximation of the L4-5 disc.
Figure 12:
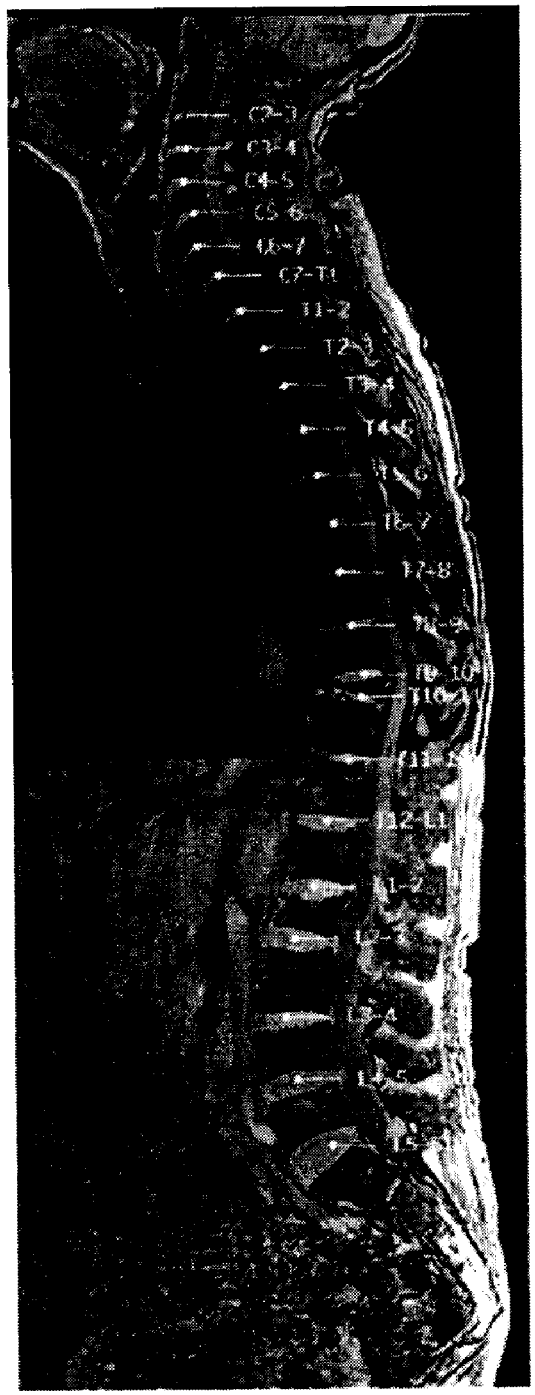
FIG. 12 is a sagittal image through the entire spine of a patient with labels generated using robust disc discrimination and Gaussian filters.

During testing, the exemplary algorithm was accurate in all 50/50 cases (100%) of the patients to include the original 27 patients plus 23 subsequent cases, despite the presence of congenital variations (FIGS. 5, 6), post-operative changes (FIG. 11), and prominent disc or vertebral pathology (FIG. 12) in this patient population. None of the 50 cases required technologist input of more than a single interspace (C2-3) though the algorithm provides such an iterative pathway if necessary. In the vast majority of cases, the algorithm 100, running on a personal computer with a 2.8 GHz processor, took less than 2 minutes to identify and label all intervertebral discs or vertebrae.

Although the ASSIST algorithm 100 was successful in all 50 patients studied, the 7 section sagittal acquisition might be insufficient for some patients. For examples, it might be expected to fail in subjects with severe scoliosis due to insufficient spine coverage. As such, if significant scoliosis is suspected, more sagittal sections could be auto-prescribed, the cost being a proportionate increase in scan time. The automated disc detection/numbering algorithm 100 was designed to accept any number of sagittal sections, and so is potentially applicable to other populations in addition to the adult population which was used to test the exemplary embodiment described above. An alternative method of accommodating additional populations is to modify the disc constraints and parameters, described above, before using the algorithm to identify spinal structures in those populations.

While the illustrative disc detection algorithm 100 described above requires manual input of the most cephalad disc, C2-3, to achieve maximal accuracy, it should be appreciated that automated computer detection of this interspace may be implemented. The C2-3 disc may be readily discerned on midline sagittal head images with a 22-24 cm FOV, (as described in 2004 at pages 233-37 of volume 25 of the American Journal of Neuroradiology and in 2003 at pages 922-29 of volume 24 of the American Journal of Neuroradiology, the teachings of which are incorporated by reference) or ASSIST 35 cm FOV cervico-thoracic spine images based on several unique features. These include the characteristic shape of the C2 vertebrae and relatively constant relationship to the skull base and cervico-medullary junction.

The illustrative algorithm above may be modified to enhance robustness over a wider range of populations, modalities and scan sequences. For example, rather than initially searching for discontinuous structures, (intervertebral discs or vertebral bodies) a MRI algorithm might instead search for the continuous relatively midline and predominately vertically oriented tube-like spinal cord extending from the brainstem to the conus and ending at approximately the L1 level; and a CT-optimized algorithm might search for the non-bone containing spinal canal extending from the foramen magnum (large opening at the skull through which the brainstem passes as it transitions to the cervical cord) to the sacrum. For MRI, the algorithm could continue caudal from the conus by searching for the fluid-filled spinal canal extending to the sacrum. A region growing algorithm such as "regiongrow" (MATLAB) might be employed starting from the readily identifiable brainstem (with MRI) or foramen magnum (with CT) and followed caudal to the sacrum. The idea is to start with a set of "seed" points and from these grow regions by appending to each seed neighboring voxels with predetermined properties similar to the seed.

Once the course of the spinal cord or canal is identified the search for intervertebral discs or vertebral bodies could be favorably constrained to the appropriate region immediately anterior to the cord/canal and the orientation of the putative intervertebral discs and bodies could be constrained so that they are nearly perpendicular to the long axis of the cord/canal at each level.

Figure 13A:
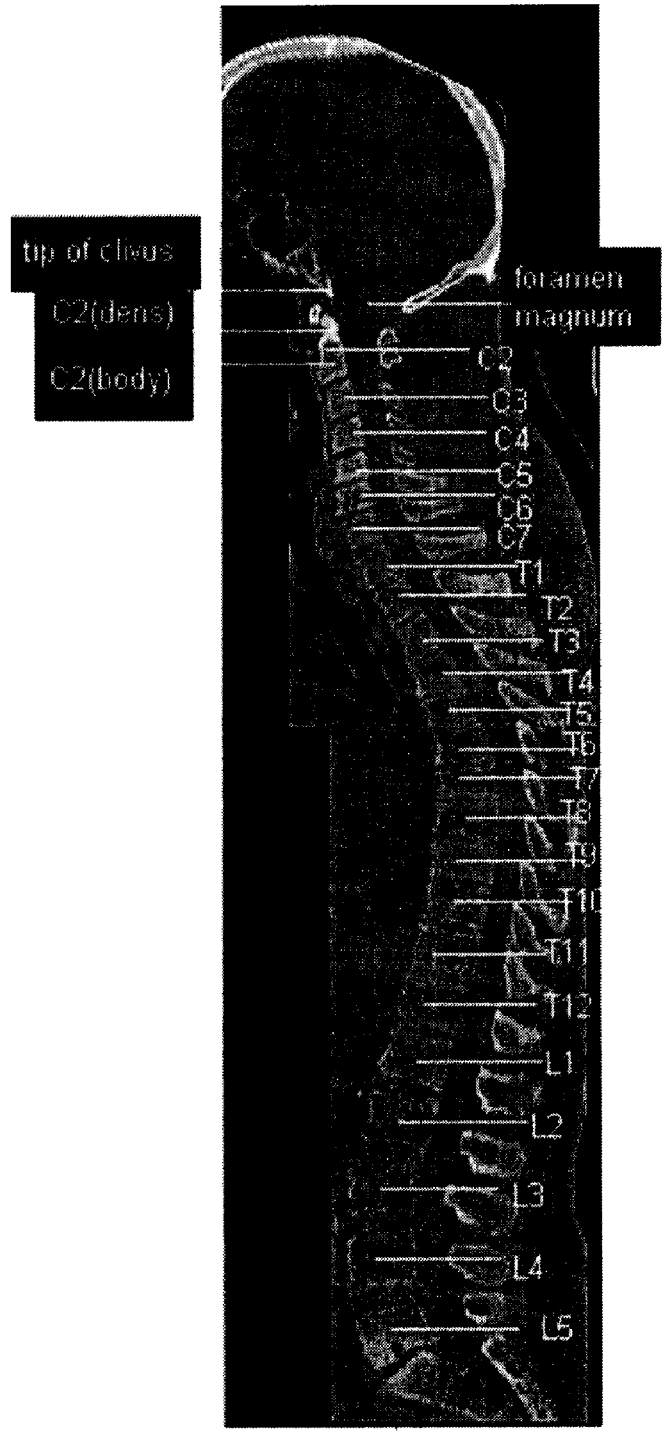
FIG. 13a is a midline sagittal image through the skull and entire spine of a patient auto-generated from a volumetric CT data set with correctly labeled vertebrae using the Automated Spine Survey Iterative Scan Technique (ASSIST) algorithm described herein in the context of MRI spine images. Bone optimized reconstruction algorithm utilized and contrast settings also optimized for bone depiction.

Alternatively or additionally, the algorithm could iteratively search for and identify structures from the head caudally to the sacrum. In FIG. 13a for example, the algorithm could first locate the tip of the clivus (anterior aspect of the foramen magnum). As is well known to those of ordinary skill in the art, the head (brain and skull) is a well characterized rigid body, and auto-identification of head structures can be readily achieved on 2D midline sagittal sections or lateral projections (as described in Weiss K L, H. P. Computer Automated Three-Step (CATS) Program for Brain MRI Prescription in Talairach Space. US Office of Patent and Copyright. USA: University of Cincinnati, 2004; Weiss K L, Pan H, Storrs J, et al. Clinical brain MR imaging prescriptions in Talairach space: technologist- and computer-driven methods. AJNR Am J Neuroradiol 2003; 24:922-9 and Weiss K L, Storrs J, Weiss J L, Strub W. CT brain prescriptions in Talairach space: a new clinical standard. AJNR Am J Neuroradiol 2004; 25:233-7.) or from 3D volume data sets, the latter method often employing referential atlases, volumetric matching, and probabilistic determinations (Auto-Align, Cortechs Labs Inc., Charlestown, Mass.; SPM, Wellcome Dept. of Imaging Neuroscience, London, UK; FSL, Analysis Group FMRIB, Oxford, UK).

After auto-locating the tip of the clivus, the algorithm could then search for C2 (dens and body) situated in very close proximity beneath the clival tip. After identifying and perhaps outlining the C2 body, the algorithm could search for the adjacent disc (C2-3) or vertebra (C3) and continue this iterative process caudally until the sacrum is identified. As each vertebra and/or disc is consecutively identified, search parameters for the next level can be modified based on the size and orientation of previously identified structures (vertebrae and discs).

As disclosed for MRI and CT of the brain in the cross-referenced application, direct scanner integration and related algorithms for computer assisted diagnosis could eventually be used in "real-time" automated spine image analysis and iterative scan prescriptions. For example, with MRI, optimally angled axial oblique sequencing could be auto-prescribed through all interspaces or those discs demonstrating abnormal morphology or signal characteristics on the ASSIST or subsequent sagittal sequences. Specific Absorption Rate (SAR) limitations set by manufactures, FDA, or similar international regulatory bodies to reduce body or body part heating may also be mitigated by an algorithm to optimize the order of auto-prescriptions (regions to be covered) so as to allow time for cooling of one region while scanning another. By streamlining and converting Matlab code to C++, algorithm processing time might be significantly shortened. Coupled with an integrated head and spine array coil, rapid computer automated iterative prescription and analysis of the entire neuro-axis may be possible.

Alternatively, or additionally, 3-D sagittal spine sequencing may be obtained. This a volumetric MRI data set or a volumetric CT data set could then be automatically reformatted in optimized planes for visualization of anatomy and pathology with discs and vertebrae accurately labeled. Typically, the three chosen orthogonal planes would be oriented relative to the patient's spinal axis as derived with ASSIST algorithm 100, or modification thereof, rather than conventional auto-generated sagittal, axial, and coronal planes oriented relative to the scanner.

Figure 13B:
FIG. 13b displays the same midline sagittal section through the skull (brain) with "standard" soft tissue-optimized reconstruction algorithm utilized and contrast settings optimized for brain depiction.
Figure 13C:
FIG. 13c displays the same midline sagittal section through the skull (brain) with composite auto-display of the optimized bone (skull) from FIG. 13a and the optimized soft tissue (brain) from FIG. 13b.

In regards to CT or other potentially volumetric imaging techniques, after acquisition of the initial volumetric data set, the ASSIST computer algorithm could be used to prescribe additional sections through specific areas of interest, with different imaging parameters (e.g. kVp, mAs, slice thickness or helical acquisition technique) or in a dynamic mode post contrast administration. Moreover, ASSIST may be used to optimize the reconstruction algorithms (block 6) or field-of-view (FOV) utilized after acquisition of the volumetric data set. For example, in relation to spine imaging, FOV centering or size may be adjusted so as to focus on the spinal elements. A bone-optimized algorithm could be chosen for sections containing bone (e.g. axial oblique sections through the vertebral bodies) and a soft-tissue algorithm could be chosen for sections containing soft tissues (e.g., discs, or the brain as shown in FIG. 13b). Furthermore, composite images may be created such that regions containing bone are displayed with the bone algorithm and those without bone are displayed with the soft-tissue algorithm (FIG. 13c). Additionally, once an algorithm such as described previously has been used to identify bones and soft tissues, those bones and soft tissues can be displayed with independent contrast settings such that the features of the bones and soft tissue are optimally visible. Further, the contrast settings for bones and soft tissues could be independently adjustable, so that a doctor, technologist or other individual examining a reconstructed image could adjust the contrast of the various portions of the image to suit their purposes and preferences.

Another use for detection and labeling algorithms such as described above is the automated production of reports. For example, at the present time, a neuroradiologist examining a picture of a patient's neuro axis can write notes such as that the canal is stenotic (tight). However, utilizing the algorithms described above, a computer can automatically identify various features of the neuro axis, and then write summary reports regarding those features which are much more detailed and clear than is currently possible. For example, the algorithms described above could identify the location of the canal, and produce a report which includes both the precise canal volume and an indication of its relationship to the average canal volume in terms of standard deviations. Similar information could be produced and expressed for any portion of, or structure in, the neuro axis.

In conclusion, the entire spine can be effectively surveyed with sub-millimeter in-plane resolution MRI or volumetric multi-detector CT in less than 1 minute. All C-T-L vertebrae and discs can be readily identified and definitively numbered by visual inspection or semi-automated computer algorithm. We advocate ASSIST for all thoracic and lumbar spine MRI studies, as well as all MRI or volumetric CT studies which include the entire cervical, thoracic, and lumbar spine. This rapid technique should facilitate accurate vertebral numbering, improve patient care, and reduce the risk of surgical misadventure. The ASSIST computer algorithm may be modified to provide iterative patient-optimized MRI or CT scan prescriptions through regions of suspected pathology as well as optimized multiplanar reconstructions, display and labeling of volumetric MRI or CT data sets.

Integrated Multimodality, Multi-Functional Spatial Reference and Skin/Surface Marking System.

With or without internal structures labeled, there are a number of advantages to providing an external skin/surface marking system. There are three major configurations of the device as follows: (1) a point localizer, (2) cross-shaped localizer grid, and (3) full planar localizer grid/phantom.

In one version, the point localizer 500 of FIGS. 14A-14I includes a detectable region affixed to an adhesive fabric strip with corresponding markings so that after application and imaging the localizer can be removed with skin marking remaining. It should be understood that the detectable region is the portion of the localizer that generates an identifiable representation in a medical diagnostic image. As will be discussed below, a detectable region is preferably, though not necessarily, multimodality compatible. The localizer can also directly adhere to the skin. Alternatively, an ink or dye could be added to the adhesive/undersurface of the localizer to directly mark/imprint the skin obviating the fabric strip. For MRI and CT a detectable region could comprise a small loop of tubing which could be filled with a radioattenuative solution (e.g. containing iodine) doped with a paramagnetic relaxant (e.g. $CuSO_4$, $MgSO_4$, Gd-DTPA). Alternatively, the tubing itself may be radiopaque for optimal CT visualization. For nuclear imaging to include planar scintigraphy, SPECT and PET, the detectable region might include a port to allow filling with the appropriate radionuclide. While the above localizers would be visible with planar radiography, a fine wire circle or dot (e.g. lead, aluminum) could also be utilized as a detectable region with this modality given its very high spatial resolution. Other shapes and corresponding adhesive markings could be utilized to discriminate different foci and/or add further localizing capability. Additionally, an activatable chemiluminescent mixture could be added for thermography, optical imaging, light based 3D space tracking or simply improved visualization in a darkened environment.

In the second major detectable region configuration, a unique cross shaped grouping of prefilled or fillable tubing is utilized as a grid for cross sectional imaging with the number and position of tubes imaged in the axial or sagittal planes corresponding respectively to the slice's z or y distance from the center. In this configuration, each tubing might be constructed as a different section of the detectable region. For planar radiography, a flexible radiopaque ruled cross shaped grid can be employed as a detectable region. Both grids are removable from similarly ruled cross shaped adhesive strips after patient application and imaging.

As a third example of a detectable region, a unique essentially planar grid/phantom is described which may be of flexible construction and reversibly affixed to an adhesive/plastic sheet with corresponding grid pattern for skin marking and to serve as a sterile interface between patient and reusable grid/phantom. The grid/phantom may also be directly adherent to the skin for guided aspiration or biopsy with the cross sectionally resolvable spatial reference in place. A diagonally oriented prefilled or fillable tube overlies a grid like lattice of regularly spaced tubing so that slice location and thickness can be readily determined in the axial and sagittal planes. Additionally, the spatial accuracy of the imaging modality could be assessed and, if individual tubes are filled with different solutions, as might be the case in instances where the different tubes are different sections, multipurpose references for MR/CT, and nuclear imaging could be achieved. Furthermore, if the tubing is surrounded by a perfluorocarbon or other uniform substance without magnetic susceptibility, MR imaging could be improved by reducing skin/air susceptibility and motion artifact. Additionally, the grid/phantom could be incorporated in routinely utilized pads and binding devices with or without skin adhesion and marking.

Figure 14G:
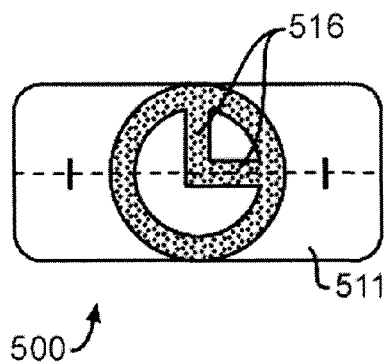

Returning to the drawings, FIGS. 14A-14I depict an illustrative version of a point localizer 500. In FIG. 14A, a loop of prefilled tubing 510 (i.e., a tubal lumen shaped into a tubal ring) is shown superimposed on and reversibly affixed to an underlying medical grade fabric 511, which may double as an adhesive bandage to both cover and mark a wound or puncture site. The diameter of the tubular ring 510 may be 2 cm mid luminal, as illustrated, or outer luminal, as perhaps preferable for integration with the cross shaped grid configuration. Other sized rings, to include in particular a 1 cm. diameter, may also have merit. The tubal lumen should measure 2-5 mm in cross sectional diameter. Cross sectional images through the ring will have characteristic and quantifiable appearances depending on slice thickness and distance from the center. A thin slice through the loop's center, for example, would demonstrate 2 circles of luminal diameter whose centers are separated by a distance equal to the ring's diameter.

The tube lumen can be filled with an appropriate concentration of an iodinated contrast agent for optimal CT visualization doped with a paramagnetic relaxant such as $CuSO_4$, $MgSO_4$, or GdDTPA to maximize MRI signal via preferential T1 shortening. Alternatively, the tubing itself may be optimally radiopaque for CT, obviating the iodinated contrast. If desired, for optical imaging, thermography, light based 3D space tracking, or improved visibility in a darkened environment, one could add an activatable chemiluminescent mixture whose critical reagents are separated by a membrane readily breached by external force applied to the ring.

A slightly redundant backing 512 is provided for the adhesive side of the fabric 511 to facilitate peeling (FIG. 14B arrows) and skin placement. With backing 512 removed, the unit 500 adheres to skin 513 as depicted in FIG. 14C. After imaging, the loop 510, which has its own adhesive undersurface, may be removed revealing an underlying fabric marking 514 as in FIG. 14D. The upper surface of the fabric, or circumscribed area thereof, may also have adhesive backing-like properties to facilitate detachment of the loop 510. Once separated from the fabric, the loop 510 could also directly adhere to the skin 513 as in FIG. 14E. Additionally, the adhesive undersurface of the ring could contain a medical grade dye or ink so that a corresponding imprint would be left on the skin 513 after removal, potentially obviating the fabric marker.

A port 515 may be directly integrated into the tubular ring 510 as in FIG. 14F, and a vacuum created within the lumen to facilitate filling at the imaging center. This feature could be beneficial for radionuclide scans and add flexibility for other imaging studies. Alternatively, the detectable region might comprise a virtual space within a composite plastic sheet. Such a detectable region could be created by adhering two plastic sheets to one another, but allowing a region of sheets (the virtual space) to remain separable so that it could later be filled in a manner similar to the tubing discussed above. Such use of a virtual space would not require the manufacture with a vacuum, because a virtual space, unlike a tube, does not ordinarily have any contents.

Figure 14H:
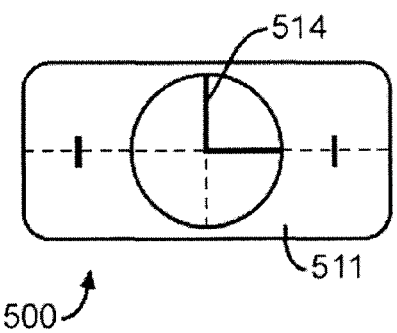

To increase spatial reference capability and allow multiple localizers to be discriminated from each other, the detectable regions such as the ring and underlying fabric marking may be modified as in FIGS. 14G and 14H. As illustrated, two tubular spokes 516 at right angles to each other may be added with luminal diameter less than or equal to that of the loop. Typically, the modified ring would be positioned on the patient so that the spokes are aligned at 0 and 90 degrees as perhaps determined by the scanner's alignment light. Subsequent rings could be progressively rotated 90 degrees so that quadrants I, II, III, and IV are sequentially subserved by the spokes. With the simple ring included, this would provide 5 distinguishable localizers. Moreover, if stacking of two rings is utilized, 30 (5×6) distinguishable localizer configurations are possible. Suggested numbering would employ the base 5 system, assigning the simple ring the value 0 and each modified ring the value of the quadrant subserved.

Figure 14I:
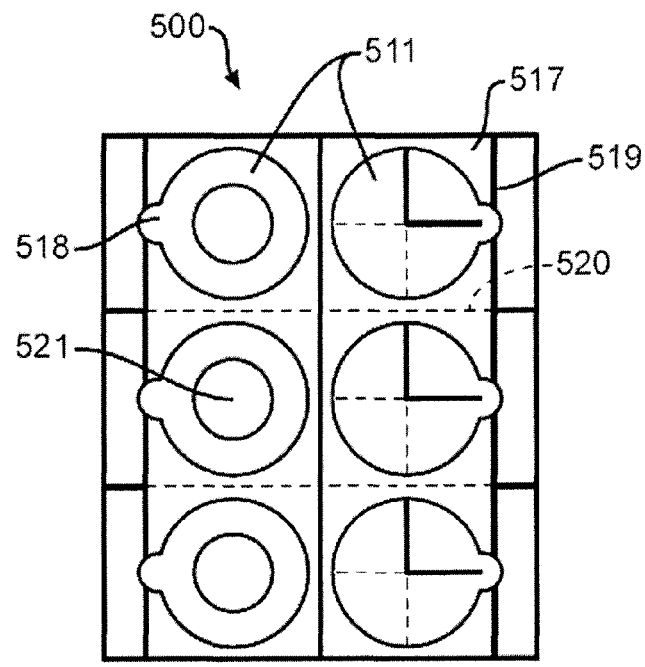

Multiple localizers may also be dispensed on a single sheet rather than individually packaged. FIG. 14I illustrates such a sheet, demonstrating adhesive backing 517 and overlying fabric 511 with the simple ring (left side) and modified ring (right side) localizers removed. Tabs 518 have been added to the fabric to facilitate both removal of the unit from the backing and the localizer from the fabric. Discontinuity of the backing (solid lines 519) underlying the tabs would also simplify removal of the fabric from the backing and perforations through the backing (dotted lines 520) would facilitate separation of individual units from each other. If desired, a smaller diameter (e.g. 1 cm) ring and associated backing albeit without tab could be placed within the central space (521) bordered by the simple ring fabric 519.

Figure 15A:
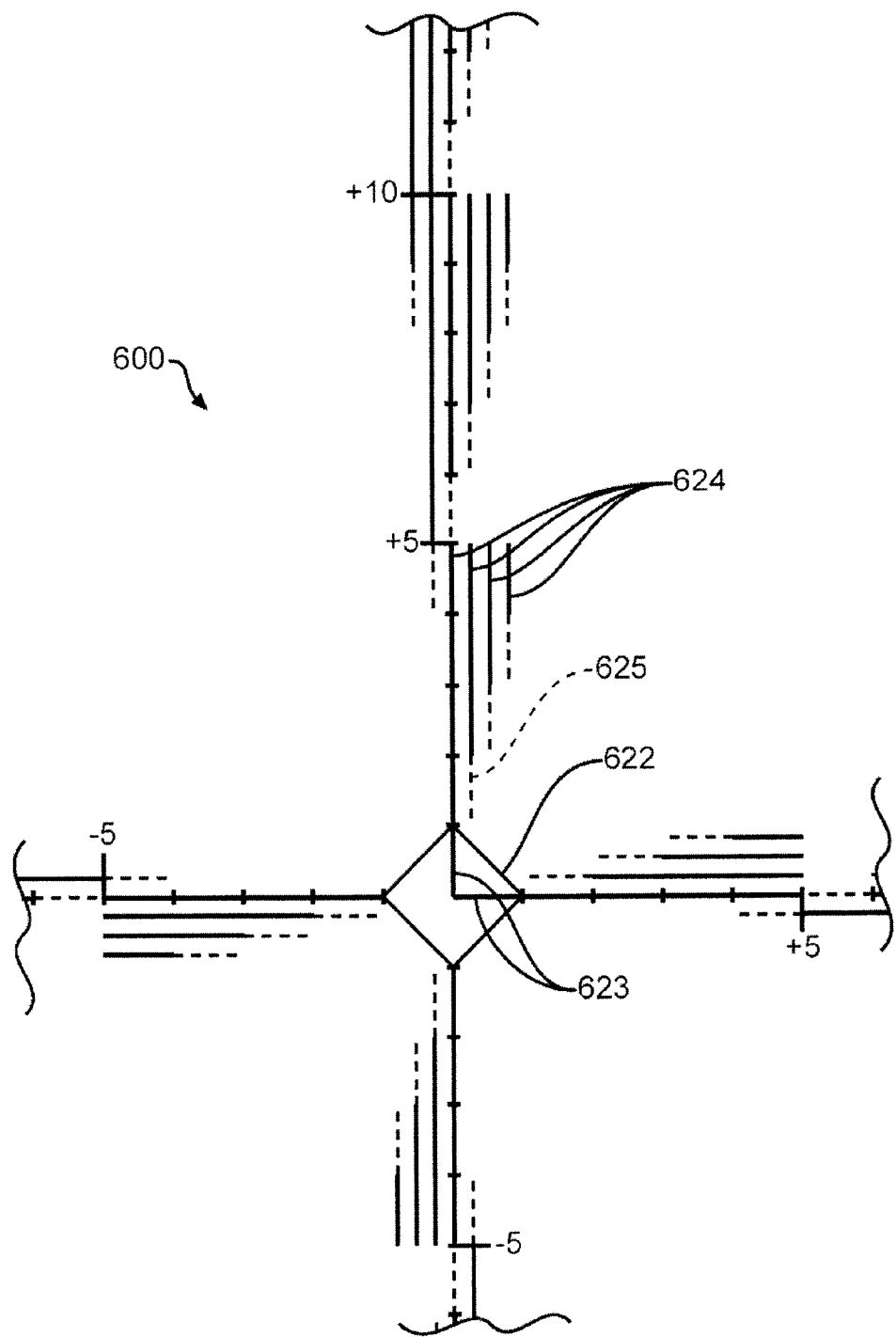

Embodiments of a prefilled or fillable cross shaped localizer grid 600 are illustrated in FIGS. 15A-15F. In FIG. 15A, a modified tubular square 622 with diagonal dimensions of 2 cm and containing 2 smaller caliber spokes 623 at right angles to each other serves as the hub. Uniquely positioned rows of tubing (624) radiate from each corner along the vertical and horizontal axes. The luminal diameter of the radiating tubes is uniform and on the order of 2 mm except where indicated by dotted lines 625 corresponding to gradual tapering from 0 to the uniform diameter. Depending on the distance from the central hub, 1 or 2 rows of tubing will be present with up to 4 tubes in each row as best illustrated in a table of FIG. 15B. The lower row of tubes (i.e. closest to skin) would correspond to increments of 1 cm and the upper row to increments of 5 cm so that a maximum distance of 24 cm would be denoted by 2 full rows. To indicate positive distances, the tubes are progressively ordered from left to right or down to up with the reverse true for negative distances as illustrated in FIGS. 15A-15B. Fractions of a centimeter would be indicated by the diameter of a cross section through a tapered portion of tubing divided by the full uniform diameter.

Figure 15C:
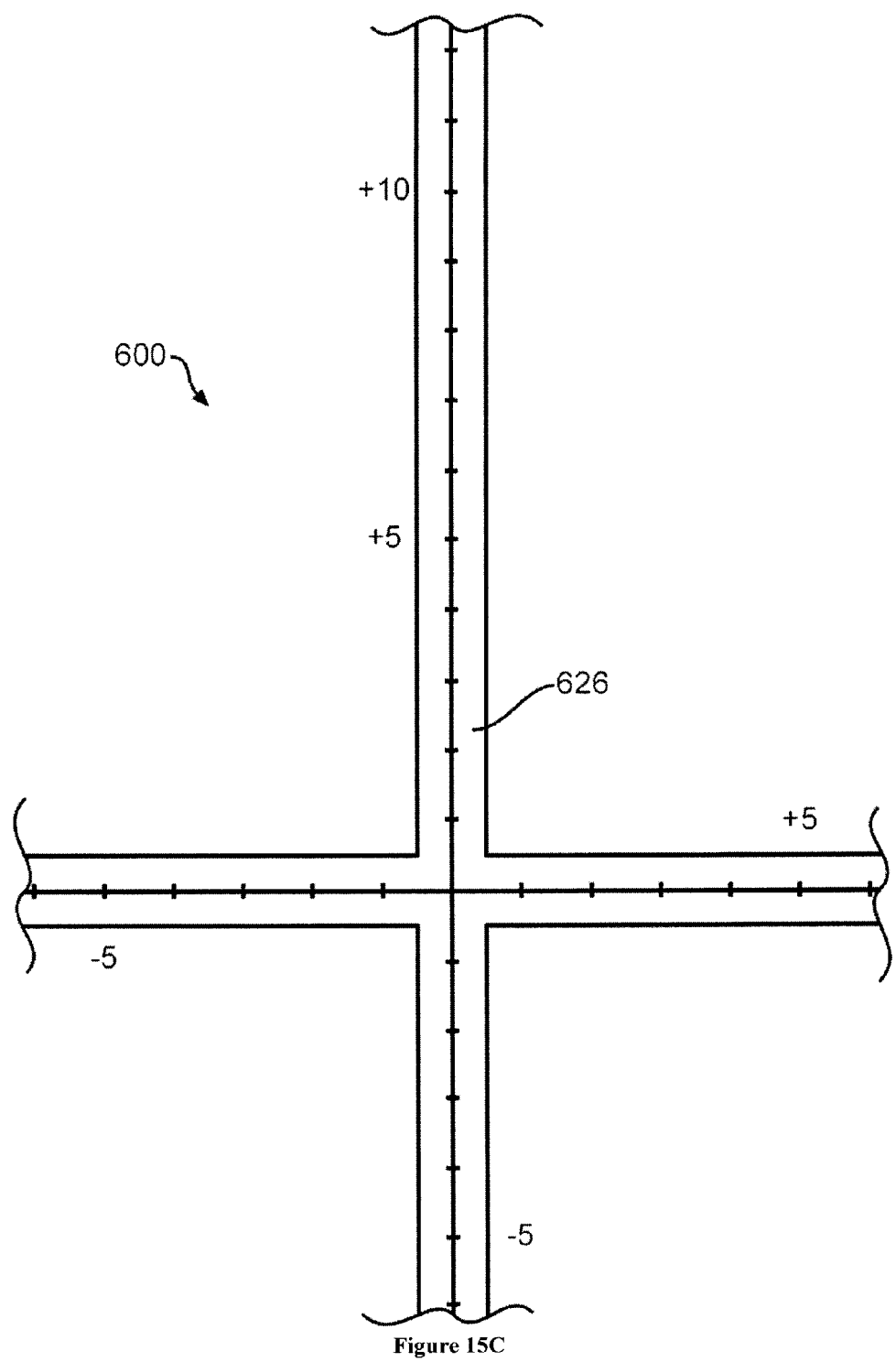

The cross-shaped grid of tubing is reversibly affixed to a medical grade adhesive fabric 626 with corresponding markings and backing. The fabric 626 is illustrated in FIG. 15C with the overlying tubing removed. The grid and associated fabric may come as a single cross-shaped unit or as a modified square and separate limbs which could be applied to the patient individually or in various combinations. Modified squares could also link whole units and/or individual limbs together to expand coverage, with 25 cm. spacing between the center of adjacent squares. The tubing may be flexible to allow the limbs to conform to curved body contours such as the breast. Additionally, either the limbs could be readily truncated at 5 cm. intervals or be available in various lengths for optimal anatomic coverage.

Figure 15D:
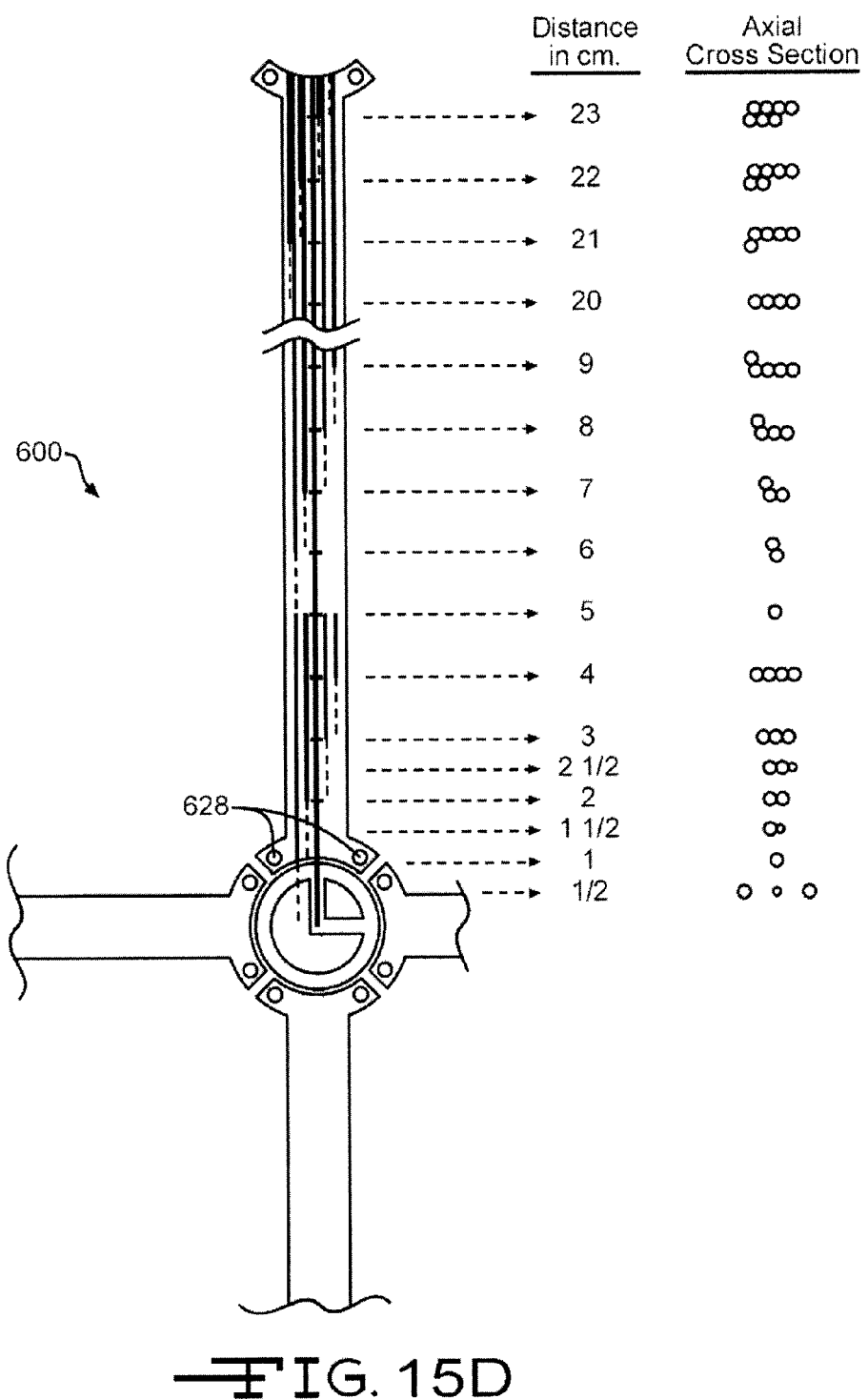
Figure 15E:
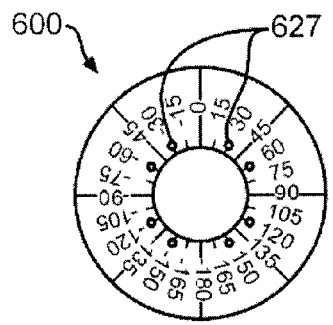
Figure 15F:
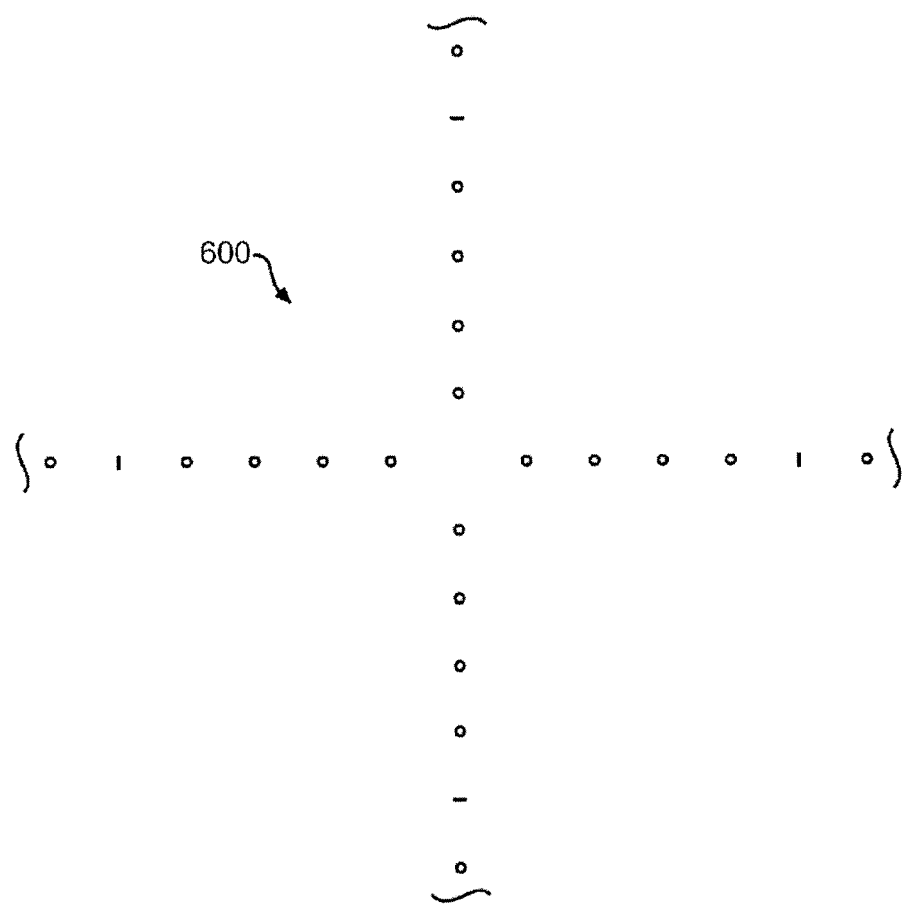

To add further utility and integration with the previously described point localizers, a modified ring may serve as the hub of the cross-shaped grid with associated modification of the limbs as illustrated in FIG. 15D. The orthogonal limbs would not have to maintain a coincident relationship to the spokes as with the modified square hub. Rather, by first placing and rotating a calibrated ring adapter (FIG. 15E) about the modified loop, 1 to 4 limbs could be readily positioned at any desired angle relative to the spokes. Pairs of male plugs 627 extending from the ring, adapter would fit securely into corresponding holes 628 at each limb base to ensure proper positioning. It is foreseen that one would typically align the modified ring's spokes with the scanner's axes and the ring adapter/limbs with the axes of the body part to be studied. By noting the chosen angulation marked on the ring adapter, optimal scanning planes might be determined prior to imaging.

For planar radiography, the detectable region might comprise a cross-shaped grid of radiopaque (e.g. lead or aluminum) dots at 1 cm intervals interposed by 5 cm spaced dashes (FIG. 15E) would minimize the imaging area obscured by overlying radiopacity. The minute opacities could be reversibly affixed by clear tape to an underlying marked adhesive fabric similar to that illustrated in FIG. 15C. Alternatively, in FIG. 15F similarly spaced radiopaque dots and dashes could be dispensed reversibly affixed to a role of medical grade adhesive tape with corresponding markings. Any length of this dually marked taped could be applied to the patient to include a single dot as a point localizer.

Figure 16A:
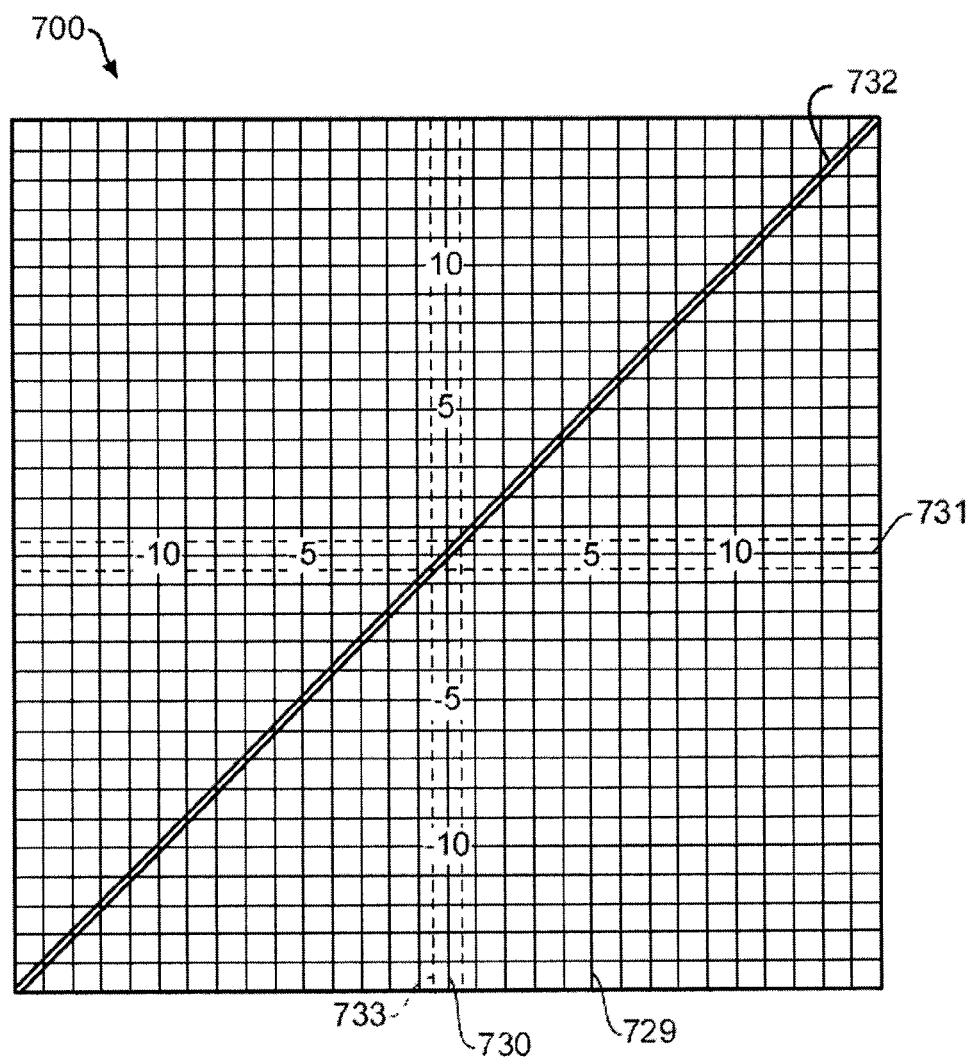
FIG. 16A is an enface view of the grid/phantom configuration with tubular lattice, overlying a diagonally oriented slice indicator, and underlying a partially adhesive fabric with markings and perforations.
Figure 16B:
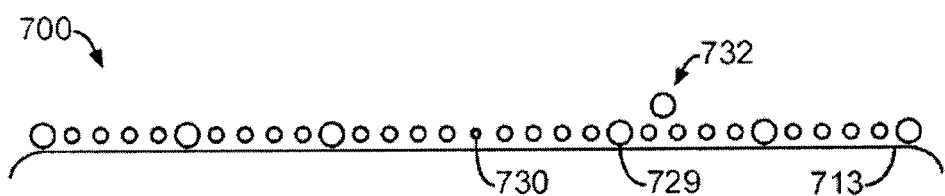
FIG. 16B is a schematic cross section of a representative axial section of the grid/phantom configuration of FIG. 16A.

In a planar localizer grid/phantom 700, 1 cm spaced horizontal and vertical tubes form a graph paper-like lattice as illustrated in FIG. 16A. Tubes at 5 cm intervals (729) would have larger luminal diameters (e.g. 3 mm) than the others (e.g. 2 mm). Central vertical 730 and horizontal 731 tubes would have a smaller diameter (e.g. 1 mm). Overlying the lattice at a 45 degree angle is a slice indicator tube 732. Depending on the distance from the horizontal or vertical axes respectively, axial or sagittal cross sections through the grid/phantom (GP) would demonstrate the slice indicator tube 732 uniquely positioned as it overlies a row of 1 cm spaced tubes. FIG. 16B illustrates a representative axial slice obtained 6½ cm above the horizontal axis. Note that the cross section of the slice indicator is positioned above and midway between the sixth and seventh tubes to the right of the sectioned vertical axis 730. Additionally, the thickness (t) of the image section can be readily determined as it equals the cross-sectional width (w) of the indicator minus the square root of 2 times the diameter (d) of the indicator lumen, $(t=w-d\sqrt{2})$.

The GP may be reversibly affixed to an adhesive/plastic sheet 713 with a corresponding graph paper-like grid for skin marking and to serve as a sterile interface between the patient and GP. Perforations 733 may be placed in the sheet as shown in FIG. 16A to allow ready separation of a cross-like ruled adhesive fabric (similar to that illustrated in FIG. 15C), from the remaining plastic sheet after imaging and removal of the GP.

The square GP can preferably be constructed to have outer dimensions equal to a multiple of 10 cm (e.g. 30 cm as illustrated) to allow for simple computation if GPs are placed side to side for expanded surface coverage. Adapters could be provided to ensure secure and precise positioning of adjacent GPs either in plane or at right angle's to each other. The GPs can be flexible or rigid in construction and be utilized with or without skin adhesion and marking.

Tubes may be filled uniformly or with a variety of known solutions having different imaging properties to serve as multipurpose references. For the latter, the 5 cm spaced tubes and slice indicator may be filled with the same optimized solution as previously described, while each set of 4 intervening tubes could be filled with different solutions in similar sequence. In this fashion, identical series of 5 reference solutions would repeat every 5 cm, allowing intraslice signal homogeneity to be assessed as well. If 9 rather than 5 different solutions are desired, sequences could instead be repeated every 10 cm. For MRI, the central tubes may also be surrounded by an oil/lipid within a larger lumen tube to serve as both a lipid signal reference and allow for measurement of the fat/water spatial chemical shift. Furthermore, if the GP tubing is surrounded by a perfluorocarbon or other substance without magnetic susceptibility, MR imaging could be improved by reducing skin/air susceptibility artifact and dampening motion. The GP may also be incorporated into a variety of nonmodality specific pads (including the ubiquitous scanner table pad(s)), binders, compression plates, biopsy grids and assorted stereotaxic devices.

Two additional variations are now described, potentially replacing the somewhat complex cross design (FIGS. 15A-15F) with an extension of the basic point localizer (FIGS. 14A-14I) or modification of the planar phantom/localizer (FIGS. 16A-16B). These changes may further simplify and unify the proposed marking system.

Figure 17A:
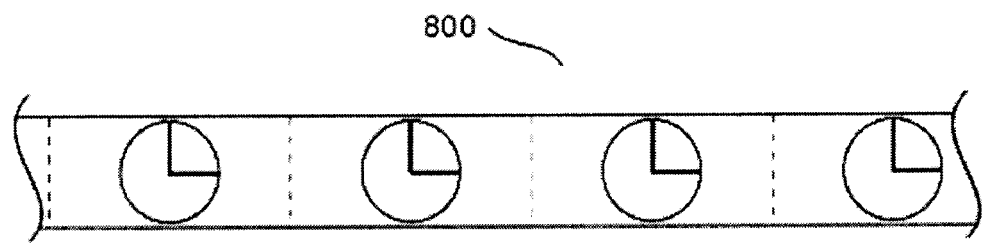
FIGS. 17A-17B are diagrams of localizers in a packaged strip or roll, regularly spaced at 5 cm or other intervals.
Figure 17B:
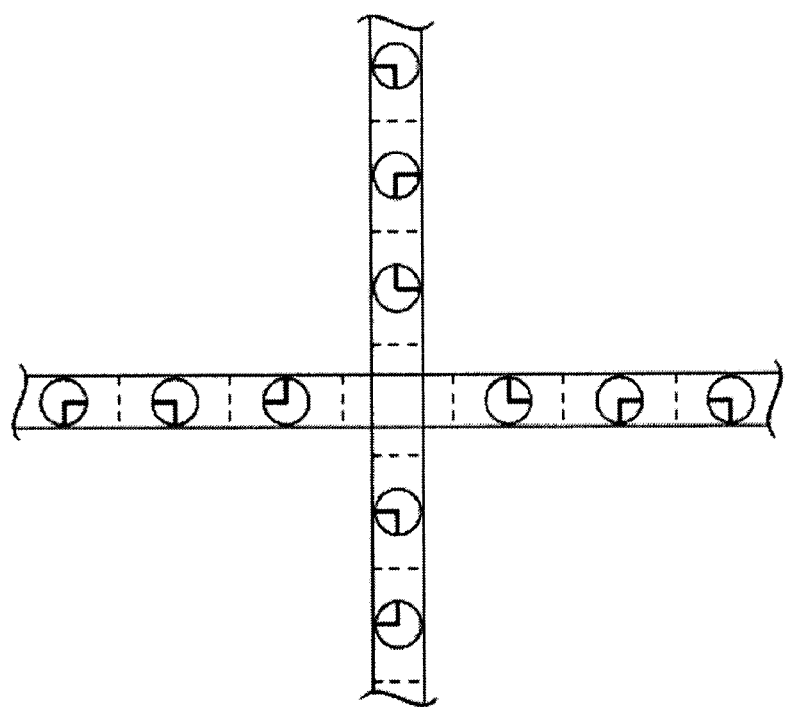

In the first instance, rather than packaging the ring localizers in a sheet as illustrated in FIG. 14I, they could be packaged in a strip or roll 800, regularly spaced at 5 cm or other intervals (FIG. 17A). The strip 800 with attached ring and/or cross localizers could then serve as a linear reference of any desired length. By placing two strips orthogonally, a cross-shaped grid is created (FIG. 17B). Individual rings can be removed from the strip or rotated to customize the grid as desired.

In the second instance, by slightly modifying the square design illustrated in FIGS. 16A-16B, an elongated rectilinear or cross configuration (FIG. 18A) is achieved consisting of linearly arranged squares extending vertically and/or horizontally from the central square. One tube in each of these squares will have a larger diameter than the other similarly oriented tubes as determined by the square's distance from the isocenter. For example, the square centered 10 cm above the isocenter would have its first tube situated to the right of midline given an increased diameter and the square centered 20 cm above the isocenter would have its second tube to the right of midline given an increased diameter and so on.

Figures 18A, 18B:
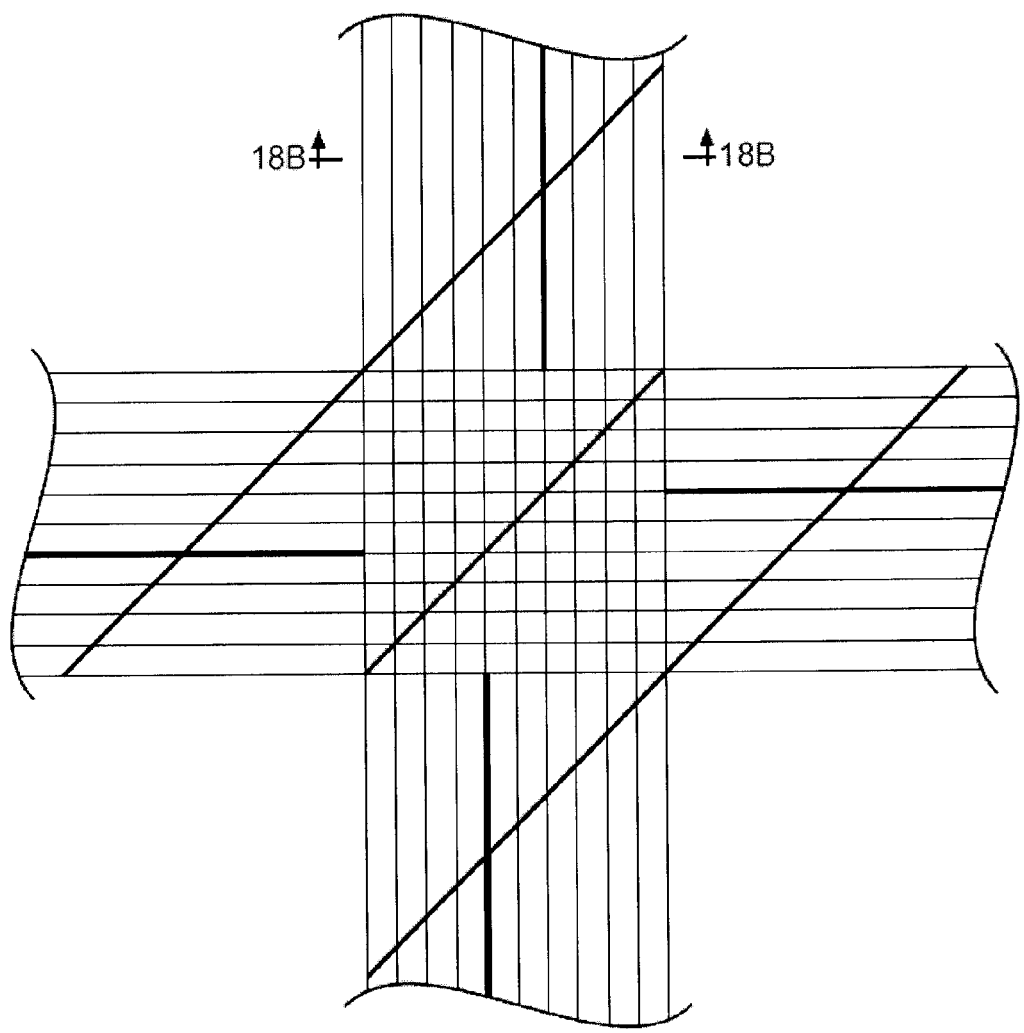
FIGS. 18A-18B are depictions of a lattice localizer having tube diameters varied to identify unique locations.

Cross sectional distance from isocenter would be read by adding the distance determined by each square's diagonally oriented slice indicator to 10 times the numberline position of the largest diameter tube. FIG. 18B illustrates the cross sectional appearance of an axial section obtained 12½ cm. above isocenter. By adding 2½ (the slice indicator position) to 10 times 1 (the tube with largest diameter), distance is readily determined.

Alternatively, the caliber of all tubes could be kept constant and instead an additional diagonal indicator tube passing through isocenter added for each elongated axis (vertical with slope of 10 and horizontal with slope of 1/10). Cross-sectional distance from isocenter would then be determined by looking at the position of both the additional and original diagonal indicator tubes in reference to the cross sectionally-created number line.

It should also be noted that localizer grids similar to those illustrated in FIGS. 16A-16B and 18A-18B could be constructed of barium (or other high x-ray attenuative material) impregnated sheets rather than tubes if computed tomography is the primary imaging modality desired and phantom attenuation values are not needed. This would significantly reduce the cost of the grid, allowing disposability and retaining 1:1 compatibility with the multifunctional tube filled grid/phantom.

Flexible Phased Array Surface Coil with Integrated Multimodality, Multifunctional Spatial Reference and Skin/Surface Marking System.

It should be further noted that applications consistent with the present invention may be modified to include a sheath for and inclusion of a flexible array MRI surface coil. Positioned vertically, this device could be closely applied to the entire cervical, thoracic, and lumbar-sacral spine. Additionally, the quantity of tubes which need to be filled in the planar configuration to uniquely denote cross-sectional positioning, has been substantially reduced from the original embodiment.

Phased array surface coils significantly increase signal to noise in MRI and are commonly employed for spine imaging. With rigid coils, patients can only be effectively scanned in the supine position, lying with the back against the coil. This results in signal drop-off in regions where the spine/back is not in close proximity to the planar coil, particularly the lumbar and cervical lordotic regions. By contrast, a flexible array surface coil would reduce the signal drop-off and allow patients to be scanned in any position. The prone position, for example, would facilitate interventional spine procedures that could not be performed with the patient supine. Patients could also be more readily scanned in flexion or extension; or with traction or compression devices. Current surface coils also lack an integrated spatial reference and skin marking system. Inclusion of the proposed spatial reference and skin marking system would facilitate multi-modality image fusion and registration as well as the performance of diagnostic or therapeutic spine procedures, such as biopsies, vertebroplasty, or XRT. Alternatively, if a coil is not constructed in a flexible fashion, it could be constructed in a contoured fashion so as to follow the natural curves of a patient's body, though this is not as preferred as a flexible array coil.

Figure 19A:
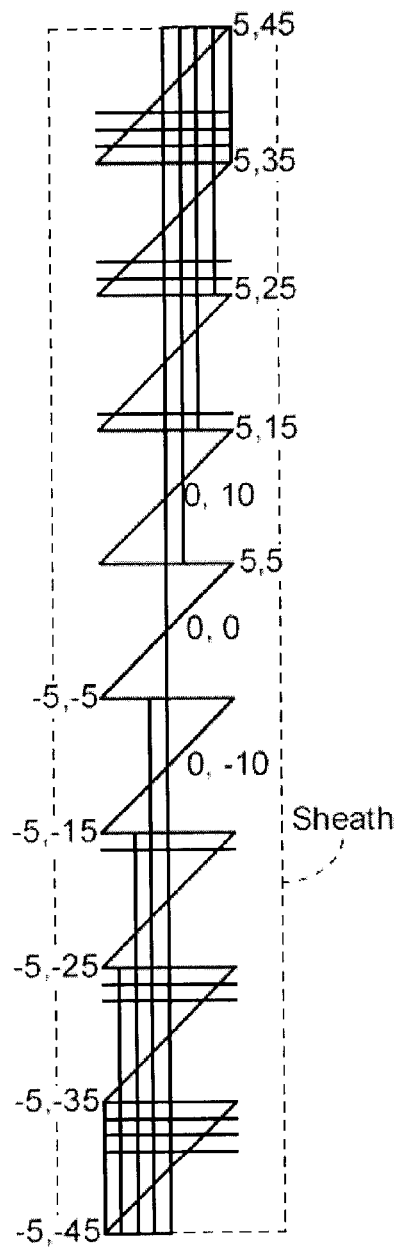
FIGS. 19A-19D are depictions of a full-spine grid localizer and multi-element array spine MRI coil.
Figure 19B:
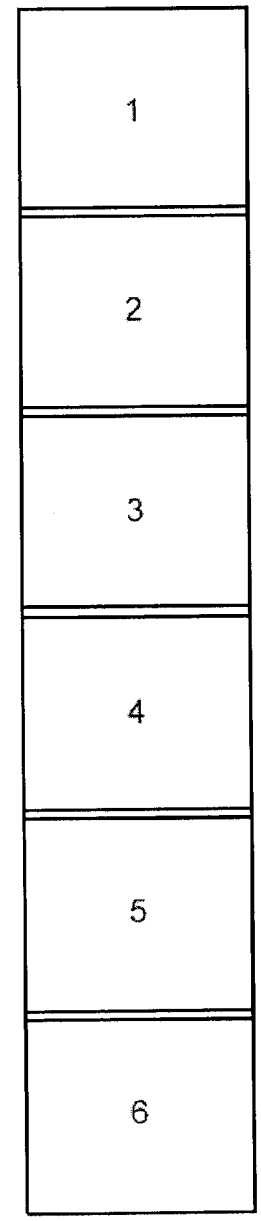

A grid-localizer sheath overlaying a coil could be adhered to the patient's spine. Tubing could be filled with a MRI readily-visible solution such as water doped with CuSO4. The grid itself would typically be 10 cm wide and 70-90 cm in length to cover the entire spine. An attached clear plastic sheath would allow introduction of a flexible array coil such as illustrated in FIG. 19B.

Figure 19C:
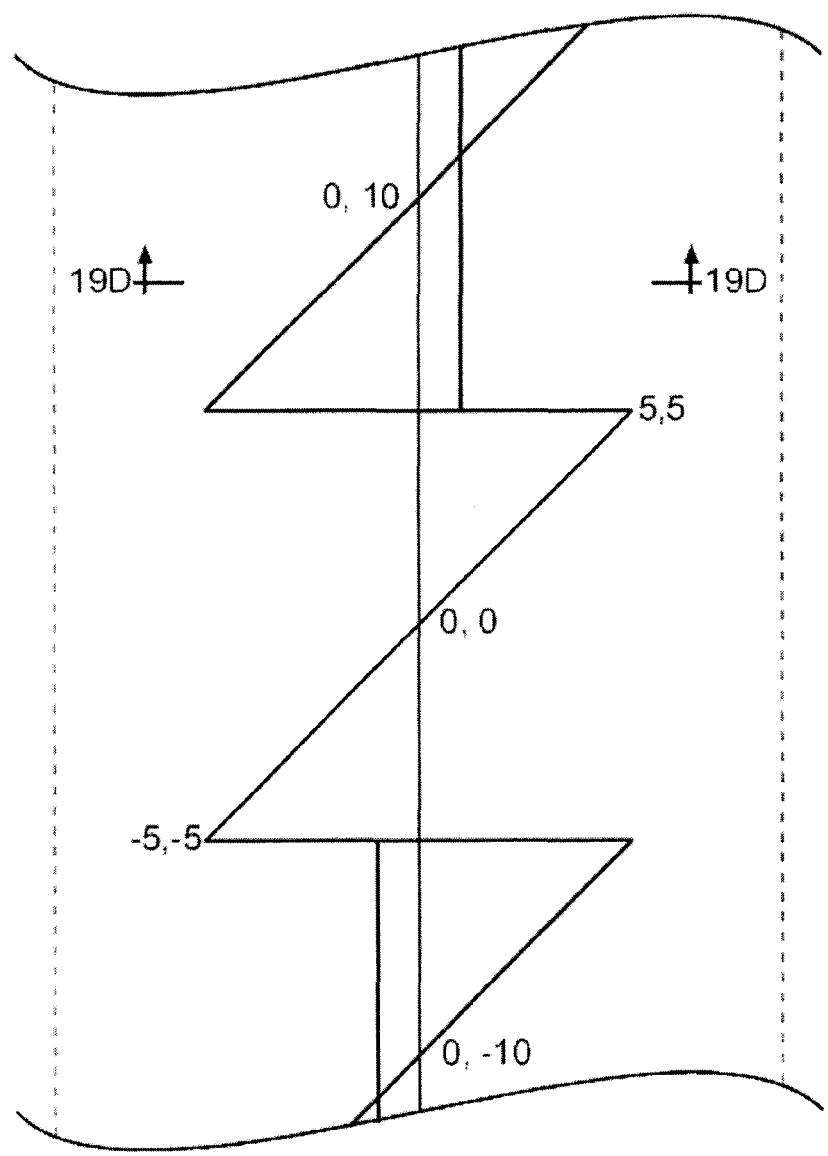
Figure 19D:
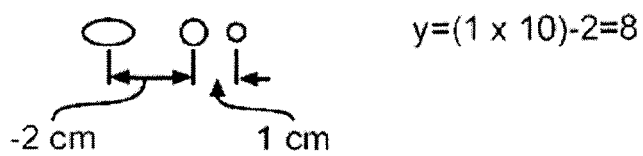

The configuration of tubing would allow unambiguous determination of the MRI scan plane (axial or sagittal) in reference to the patient's back/skin surface. The number of thin caliber tubes could denote the distance from (0, 0) in multiples of 10 cm as illustrated in FIG. 19A (those to the right or superior would be positive; those appearing to the left or inferior would denote negative distances). Alternatively, as illustrated in FIGS. 19C-19D the integer distance in centimeters from a single thin tube to the central tube could be multiplied by ten to denote distance from (0, 0). Thus, 30 cm could be denoted by a single thin tube 3 cm from the central tube rather than by 3 thin tubes as in FIG. 19A. As illustrated in FIGS. 19C, 19D, an axial slice taken 8 cm superior to (0, 0), would reveal the cross sectional tubes illustrated in 19D. The thin tube being 1 cm to the right of the central tube would denote a vertical distance of 10 cm. The diagonal oriented tube in cross-section, being 2 cm to the left of the central tube, would denote a vertical distance of −2 cm. Thus, the axial plane of section would be 10−2=8 cm above (0, 0).

Using the described reference/marking system affixed to the patient's back, a diagnostic or therapeutic procedure could be performed under direct MR guidance. Alternatively with a corresponding radiopaque grid affixed to patient's back, the patient could be taken out of MRI scanner and have the procedure done with CT or fluoroscopic guidance. In either case, procedures could be performed by hand or with a robotic arm.

In regards to MRI-guided intervention: the spine array coil, tubular grid, and grid-imprinted/affixed sheath may be designed so that the tubular grid and/or coil can be independently repositioned within the sheath to allow for unencumbered instrument insertion into the desired spine region.

The aforementioned array coil—localizer grid or parts thereof in contact with the surgical site may be designed so that they are disposable or reusable after appropriate sterilization, It should be noted that all aforementioned localizers may be made with non-liquid CT and/or MRI-visible materials rather than liquid-fillable tubing. Moreover, rather than actual tubing, corresponding virtual spaces imbedded in plastic may be advantageously employed so they can be subsequently insufflated/filled with an imaging modality visible gas or liquid.

Algorithms characterizing discs, vertebrae, and other spinal structures. Once identified with ASSIST, spinal structures can be further auto-characterized in terms of their morphology and tissue characteristics; and subsequently compared to population or individual norms to determine which structures are abnormal or in need of further imaging. Such characterization and comparison could be used in the generation of reports as described above. Labeling could be used to correlate available image data, and facilitate multi-parametric (spectral) analysis of the identified structures (regions-of-interest) to evaluate tissue characteristics. The technique can facilitate the automated scan prescriptions, real-time lesion detection, and examination tailoring such as discussed previously.

Advances in MRI to include the clinical implementation of phased array-coils including multi-channel combined head and spine coils and parallel sensitivity encoded imaging when combined with the algorithms described herein offer the potential for time and cost effective non-invasive holistic screening and detailed assessment of neuro-axis pathology, to include stroke and back pain—both leading causes of disability in the U.S.

Automated MRI Prescriptions, Detection and Analysis of Brain Pathology (e.g. Acute Stroke). Based on the teachings of U.S. provisional patent application No. 60/552,332, Weiss 2003, and Weiss 2004, Talairach referenced axial oblique diffusion-weighted images (DWI), whether prescribed by a technologist or a computer, are obtained following the initial roll and yaw corrected sagittal T2 sequence. If computer image analysis of the initial DWI sequence suggests regions of acute infarction, the basic brain protocol may be streamlined and modified to include MR angiography and perfusion sequencing. This respectively permits evaluation of the underlying vascular lesion and the detection of potential perfusion/diffusion mismatches directing emergent neuro-vascular intervention. Stroke is the leading cause of disability in this country. Because the time to emergent therapy strongly inversely correlates with morbidity and mortality, the successful implementation of the proposed computer algorithms may significantly improve patient outcome.

Automated MRI Detection, Analysis, and Guided-Intervention of Spine Pathology involving vertebrae (fractures, osteoporosis and related fracture risk, malignancy, endplate degeneration—Modic Type I, II, and III changes, facet degeneration) intervertebral discs (degeneration and herniation), spinal canal (spinal stenosis, extramedullary lesions, cord lesions or tethering) and nerve roots (compression or neoplasm) Spine pathology is a leading cause of morbidity and disability in this country. The techniques described herein will improve detection and assessment of disco-vertebral degeneration, osteoporotic and pathologic compression fractures-all potential underlying causes of ubiquitous back/neck pain in this country.

Using advanced MR imaging techniques, the entire spinal axis can be interrogated in the sagittal plane in less than a minute. With this screening data, the vertebral bodies and inter-vertebral discs can be identified and subsequently analyzed with software implementing the algorithms described herein. Based on this initial assessment, regions of suspected pathology to include vertebral fractures and disc herniations, could be further interrogated with more dedicated computer driven prescriptions to confirm and better characterize pathology. If for example, a fracture is identified, additional multi-parametric sequencing through the involved vertebrae could be obtained to determine whether the fracture was related to osteoporosis or underlying malignancy. In some embodiments, the screening data might be obtained by the use of a scout scan, or initial scan. In embodiments where a scout scan is used, regions which were further interrogated would be referred to as regions subjected to detailed scans, that is scans which obtain information not available from the scout scan.

Automated Spine MRI Assessment and Guided Intervention: The techniques described herein can be used to improve current spine screening, assessment, surveillance, and therapeutic intervention. As is known to those of skill in the art, MRI-derived parameters hold promise for improved fracture risk prediction and evaluation of degenerative spine disease (see Wehrli F W, Hopkins J A, Hwang S N, Song H K, Snyder P J, Haddad J G. Cross-sectional study of osteopenia with quantitative MR imaging and bone densitometry. Radiology 2000; 217:527-38). Unfortunately, MRI has been too time intensive and costly to justify as an osteoporosis-screening instrument. It also has lacked accurate parametric quantification of key markers related to spine degeneration and back pain. These shortcomings can be addressed by integrating MRI-derived parameters of bone quality with a novel rapid high-resolution total spine screen (ASSIST).

Figure 20A:
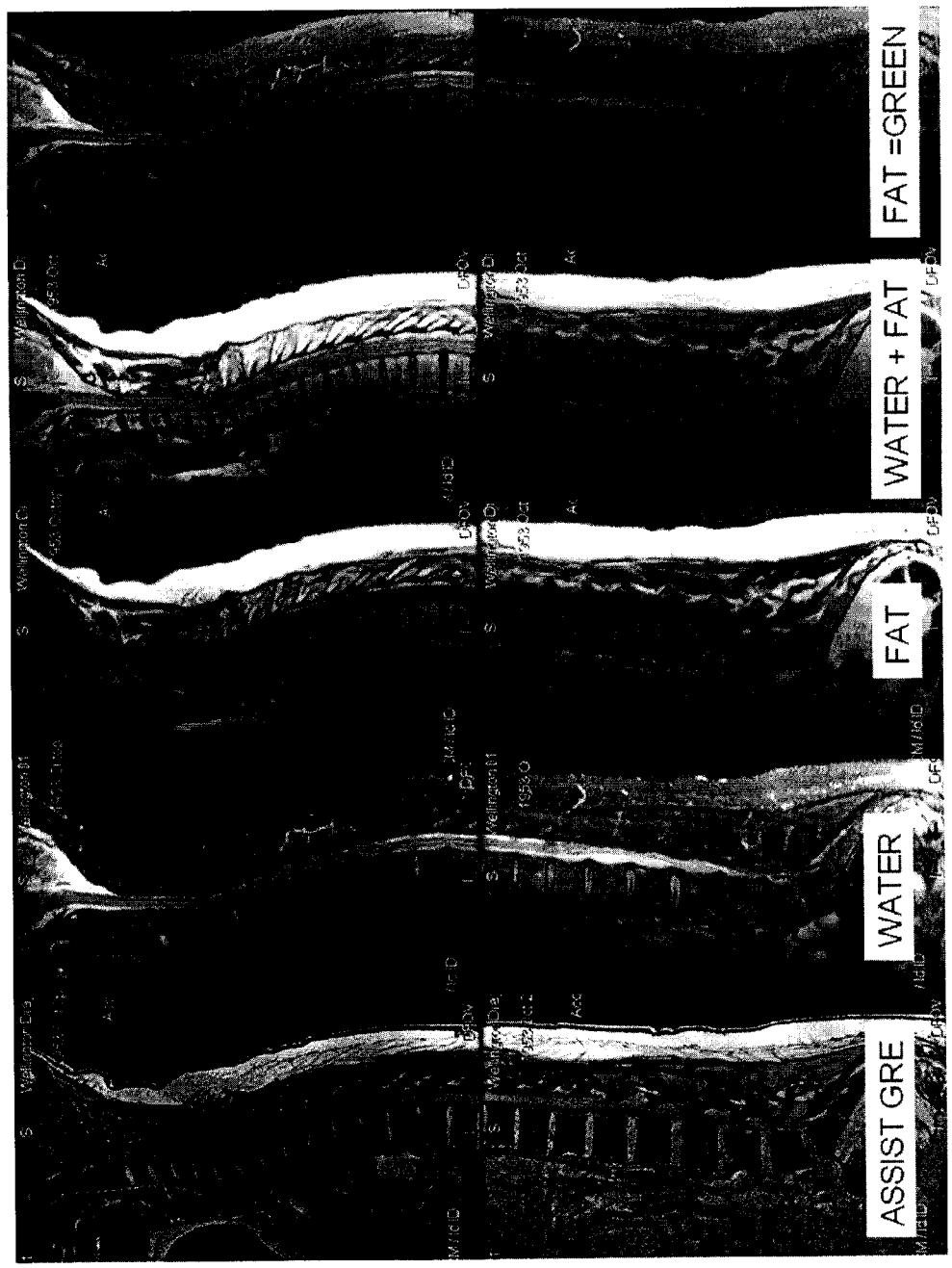
FIGS. 20A-20B demonstrate integration of ASSIST with IDEAL for improved multi-spectral tissue characterization.
Figure 20B:
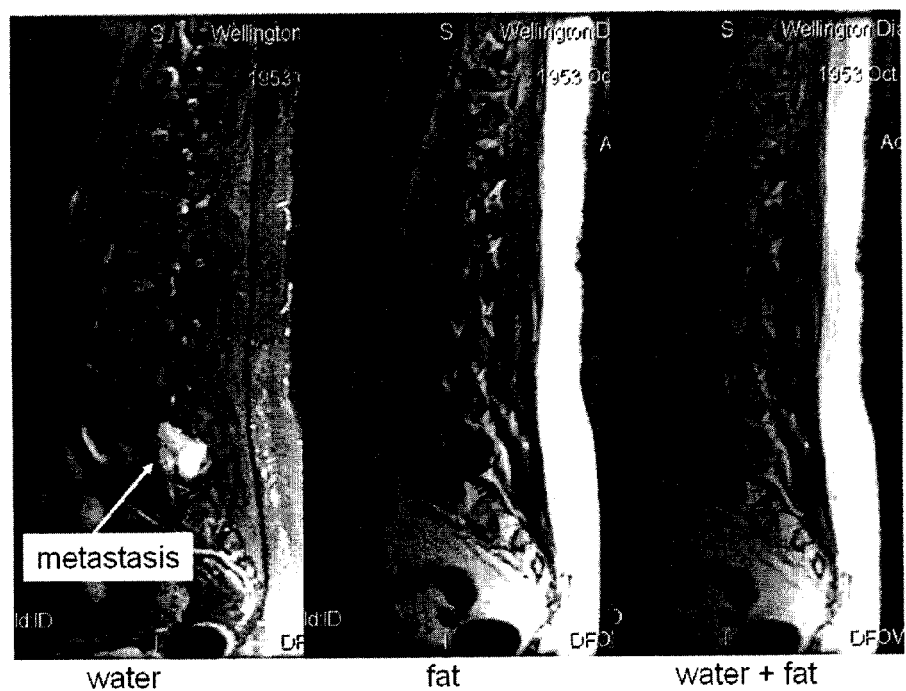
Figure 21:
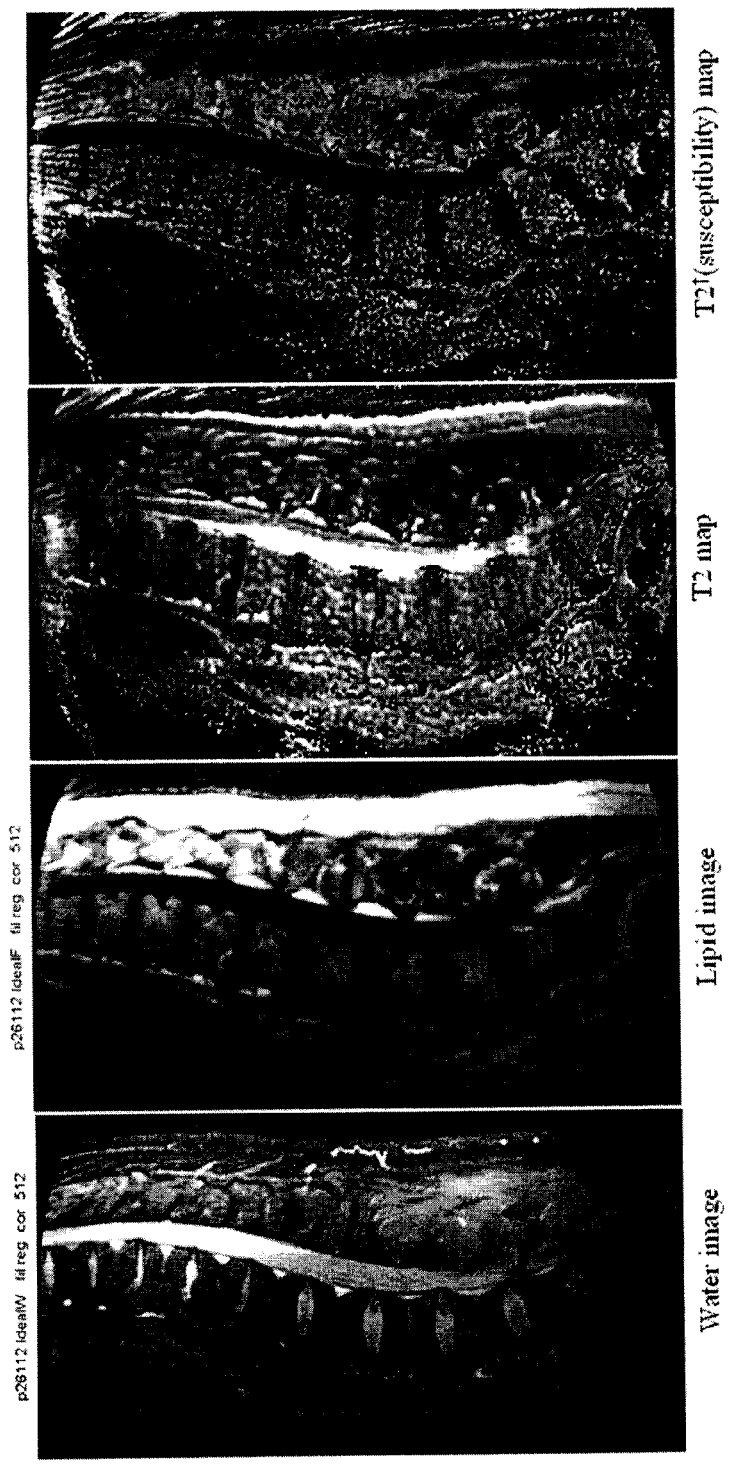
FIG. 21 depicts additional multi-parametric maps derivable from GRASE IDEAL.

In particular, the ASSIST technique described above can be integrated with fast spin-echo and GRASE (Gradient and Spin-Echo Imaging) versions of an imaging technique termed iterative decomposition of water and fat with echo asymmetric and least square estimation (IDEAL). (FIGS. 20a, 20b, and 21). The GRASE IDEAL technique provides T2, T2*, and T2$^\dagger$ maps as well as the typical water, fat, and composite (water plus fat) images. These MRI-derivable parameters may be helpful in achieving the aforementioned specific aims. For example, T2$^\dagger$ represents cancellous bone-induced intravoxel dephasing and is negatively correlated with fracture risk. Assist integrated with GRASE-IDEAL or other multiparametric derivable MRI sequences provides efficient automated screening and assessment of post-menopausal women at risk for osteoporotic or pathologic spine fractures and/or presenting with back pain.

This integration promotes patient care by providing improved risk assessment, identification and characterization of vertebral fractures; improved assessment of spine degeneration-back pain; and metastatic disease; and improved image-guided therapeutic management as well as facilitate related image-guided procedures in conjunction with a MRI-compatible robotic arm and aforementioned interventional spine array coil. The technique of integrating MRI Automated Spine Survey Iterative Scan Technique (ASSIST) can be used to provide quantitative assessment of subendplate degenerative/stress related Modic Type 1, 2, and 3 changes. Additionally, the integrated MRI Automated Spine Survey Iterative Scan Technique (ASSIST) can be used to provide quantitative assessment of fatty bone marrow replacement for early detection of metastatic disease in the spine and differentiation of osteoporotic from pathologic fractures. Further, ASSIST adaptations will enable real-time MRI-guided vertebroplasty, biopsy, and epidural injections.

What is claimed is:

1. An apparatus comprising:
   (a) a memory configured to receive a medical diagnostic image representing a neuro-axis of a patient;
   (b) a program stored in the memory and operatively configured to detect and label a plurality of spinal structures in said medical diagnostic image using an iterative process;
   (c) a processor in communication with the memory to perform the program;
   wherein the program is further operatively configured to automatically generate a prescription using said labeling of the plurality of spinal structures.

2. The apparatus of claim 1 wherein the program is operatively configured to utilize a region growth algorithm to identify a portion of the medical diagnostic image to analyze for the plurality of spinal structures.

3. The apparatus of claim 1 wherein the program is operatively configured to detect and label a spinal structure based on a landmark, and is further operatively configured to detect and label an additional spinal structure based at least in part on a previously named and detected spinal structure.

4. The apparatus of claim 1 wherein the program is operatively configured to detect and label the plurality of spinal structures based at least in part on a landmark.

5. The apparatus of claim 4 wherein the landmark is a top spinal structure.

6. The apparatus of claim 4 wherein the landmark is a seed.

7. The apparatus of claim 4 wherein the landmark is automatically detected.

8. The apparatus of claim 1 wherein the medical diagnostic image is comprised of a plurality of voxels, and wherein the program is further operatively configured to:
   (a) identify a plurality of voxels in the medical diagnostic image as candidate spinal structures;
   (b) apply a spinal structure constraint to identify a series of spinal structures comprising a subset of said candidate spinal structures.

9. The apparatus of claim 8 wherein the program is further operatively configured to detect a plurality of voxels in the medical diagnostic image as candidate spinal structures by performing a calculation comprising comparing a voxel in the medical diagnostic image with a voxel in a second medical diagnostic image wherein the second medical diagnostic image corresponds to a sagittal section adjacent to a second section corresponding to the medical diagnostic image.

10. The apparatus of claim 8 wherein the program is further operatively configured to
   (a) identify a line defined in part based on a centroid of a candidate spinal structure in the series of spinal structures;
   (b) identify an additional spinal structure by searching for a local intensity maximum along a region defined in part by the line.

11. The apparatus of claim 10 wherein the region defined in part by the line is defined in further part by extending the line based on an estimate of a position for the additional disc.

12. The apparatus of claim 10 wherein the region defined in part by the line is defined in further part by an additional line, the additional line being parallel to the line.

13. The apparatus of claim 1 wherein the medical diagnostic image corresponds to a superior portion of the neuro-axis, and wherein the program is further operatively configured to combine the medical diagnostic image with a second medical diagnostic image corresponding to an inferior portion of the neuro-axis.

14. The apparatus of claim 1 wherein the program is further operatively configured to analyze a spinal structure from the plurality of spinal structures.

15. The apparatus of claim 1 wherein the program is further operatively configured to produce a report based at least in part on the naming of the plurality of spinal structures.

16. The apparatus of claim 1 further comprising a printer operable to produce a labeled visual representation of the medical diagnostic image on film.

17. The apparatus of claim 1 further comprising a screen operable to display the labeled visual representation of the medical diagnostic image.

18. The apparatus of claim 1 wherein the prescription is to collect additional medical diagnostic images.

19. The apparatus of claim 1 wherein the prescription is for a therapeutic procedure.

20. The apparatus of claim 1 wherein the program is further operatively configured to execute the prescription.

21. The apparatus of claim 19 wherein the apparatus further comprises a therapeutic instrument and wherein the program is operatively configured to execute the prescription using the therapeutic instrument.

22. The apparatus of claim 1 wherein the program is further configured to reconstruct a slice by selectively applying a plurality of reconstruction algorithms based at least in part on the detection and labeling of the plurality of spinal structures.

23. The apparatus of claim 1 further comprising a screen wherein the program is operable to display a visual representation of the medical diagnostic image using a first contrast and a second contrast, wherein the first contrast is used for portions of the visual representation corresponding with bone and wherein the second contrast is used for portions of the visual representation corresponding with soft tissue.

24. The apparatus of claim 23 wherein the first contrast and the second contrast are adjustable.

25. An apparatus comprising:
(a) a memory configured to receive a plurality of medical diagnostic images of a patient's neuro-axis;
(b) a program stored in the memory and operatively configured to:
  (i) generate a composite midline sagittal image volume of the neuro-axis by combining two or more medical diagnostic images from the plurality of medical diagnostic images, wherein the generated composite midline sagittal image volume includes at least a portion of all interspaces and vertebrae between the patient's axis (C-2 vertebra) and sacrum; and,
  (ii) identify a plurality of spinal structures in the composite midline sagittal image volume by iteratively searching for a predefined search number of spinal structures between the patient's axis (C-2 vertebra) and sacrum, wherein the spinal structures are taken from the set of spinal structures consisting of:
    (1) intervertebral discs; and
    (2) vertebrae;
  and wherein, if the spinal structures are vertebrae, the predefined search number is 22, otherwise, if the spinal structures are intervertebral discs, the predefined search number is 23; and
  (iii) determine if a set of predefined criteria are met and, if so, allowing the predefined search number to vary by one;
(c) a processor in communication with the memory to perform the program.

26. The apparatus of claim 25, wherein:
(a) if identifying the plurality of spinal structures in the composite midline sagittal image volume comprises identifying the predefined search number of intervertebral discs, the program stored in memory is operatively configured to, after identifying the plurality of spinal structures:
  (i) based on labeling a cephalad disc from the plurality of intervertebral discs as C2-3, consecutively label the remaining discs from the plurality of intervertebral discs in a cranial-caudal fashion as C3-4 through L5-S1; and
  (ii) provide vertebrae adjacent to the plurality of discs with corresponding labels: C2 through S I;
(b) if identifying the plurality of spinal structures in the composite midline sagittal image volume comprises identifying the predefined search number of vertebrae, the program stored in memory is operatively configured to, after identifying the plurality of spinal structures:
  (i) based on labeling a cephalad vertebra from the plurality of vertebrae as C2, consecutively label the remaining vertebrae from the plurality of vertebrae in a cranial-caudal fashion as C3 through S1; and
  (ii) provide intervertebral discs adjacent to the plurality of vertebrae with corresponding labels C2-3 through L5-S1.

27. The apparatus of claim 25, wherein:
(a) identifying the plurality of spinal structures in the composite midline sagittal image volume comprises, based on labeling a top spinal structure, iteratively search for the predefined search number of spinal structures in a cranial-caudal fashion until the predefined search number of spinal structures is identified; and
(b) the program stored in memory is operatively configured to, as each spinal structure is identified, labeling that spinal structure.

28. The apparatus of claim 25, wherein:
(a) the composite midline sagittal image volume comprises the patient' head; and
(b) the program stored in memory is operatively configured to uniquely identify a plurality of head structures in the composite midline sagittal image volume.

29. The apparatus of claim 25, wherein the program stored in memory is operatively configured to perform an automated image analysis at each disc and vertebral level in patient's neuro-axis.

30. The apparatus of claim 25, wherein the program stored in memory is operatively configured to create an optimized reconstruction of a volumetric image dataset of the patient's neuro-axis based at least in part on identification of the plurality of spinal structures in the composite midline sagittal image volume.

* * * * *